United States Patent
Haning et al.

(10) Patent No.: US 6,174,884 B1
(45) Date of Patent: Jan. 16, 2001

(54) 1,5-DIHYDRO-PYRAZOLO[34-D]-PYRIMIDINONE DERIVATIVES

(75) Inventors: Helmut Haning, Wuppertal; Ulrich Niewöhner, Wermelskirchen; Ulrich Rosentreter, Wuppertal; Thomas Schenke, Bergisch Gladbach; Jörg Keldenich, Wuppertal; Erwin Bischoff, Wuppertal; Karl-Heinz Schlemmer, Wuppertal; Helmuth Schütz, Regensburg; Günter Thomas, Wuppertal, all of (DE)

(73) Assignee: Bayer Aktiengesellschaft, Leverkusen (DE)

( * ) Notice: Under 35 U.S.C. 154(b), the term of this patent shall be extended for 0 days.

(21) Appl. No.: 09/367,538

(22) PCT Filed: Feb. 26, 1998

(86) PCT No.: PCT/EP98/01086

§ 371 Date: Aug. 16, 1999

§ 102(e) Date: Aug. 16, 1999

(87) PCT Pub. No.: WO98/40384

PCT Pub. Date: Sep. 17, 1998

(30) Foreign Application Priority Data

Mar. 11, 1997 (DE) .............................. 197 09 877

(51) Int. Cl.⁷ ..................... A61K 31/519; C07D 487/04
(52) U.S. Cl. .................. 514/234.2; 514/252.16; 514/258; 544/118; 544/124; 544/131; 544/262
(58) Field of Search .................. 544/262, 118, 544/124, 131; 546/121, 164, 168, 169, 274, 286, 330; 514/258, 234.2, 252.16; 548/309.1; 549/449

(56) References Cited

U.S. PATENT DOCUMENTS

| 3,211,731 | * 10/1965 | Schmidt et al. ............... 514/234.2 |
| 3,211,732 | 10/1965 | Schmidt et al. ............... 514/234.2 |
| 4,211,731 | 7/1980 | Hofer et al. .................... 260/932 |
| 5,294,612 | * 3/1994 | Bacon et al. ................... 514/234.2 |

FOREIGN PATENT DOCUMENTS

| 11 53 023 | 8/1963 | (DE) . |
| WO 93/07149 | 9/1992 | (WO) . |
| WO 96/28429 | 3/1996 | (WO) . |
| WO 96/28448 | 3/1996 | (WO) . |
| 96 28429 | 9/1996 | (WO) . |

OTHER PUBLICATIONS

The rabbit as a model for neurourologic studies of the lower genitourinary tract, Christian G. Stief, et al., Free Paper, World Journal of Urology, Springer–Verlag 1990, 8:233–236.

Primary sequence of cyclic nucleotide phosphodiesterase isozymes and the design of selective inhibitors, Joseph A. Beavo and David H. Reifsnyder, Tips Reviews, 1990, Elsevier Science Publishers Ltd., (UK) Apr. 1990 (vol. 11) 150–155.

Identification and Selective Inhibition of Four Distinct Soluble Forms of Cyclic Nucleotide Phosphodiesterase Activity From Kidney, Mary Hoey and Miles D. Houslay, Biochemical Pharmacology, vol. 40, No. 2 pp. 193–202, 1990.

Selective Inhibition of Cyclic Nucleotide Phosphodiesterases of Human, Bovine and Rat Aorta, C. Lugnier, et al., Biochemical Pharmacology, vol. 35 No. 10, pp. 1743–1751,1986.

* cited by examiner

*Primary Examiner*—Richard L. Raymond
(74) *Attorney, Agent, or Firm*—Norris McLaughlin & Marcus P.A.

(57) ABSTRACT

The 1,5-dihydro-pyrazolo[3,4-d]-pyrimidinone derivatives are prepared by fusing the pyrimidone heterocycle with the suitably substituted pyrazoles. The compounds are suitable as active compounds in medicaments, in particular in medicaments for the treatment of cardiovascular and cerebrovascular diseases, diseases of the peripheral blood vessels and diseases of the urogenital tract.

9 Claims, No Drawings

1,5-DIHYDRO-PYRAZOLO[34-D]-PYRIMIDINONE DERIVATIVES

This application is a 371 of PCT/EP98/01086, filed Feb. 26, 1998.

The present invention relates to 1,5-dihydro-pyrazolo[3,4-d]-pyrimidinone derivatives, to a process for their preparation, and to their use in medicaments, in particular for the treatment of cardiovascular and cerebrovascular diseases, diseases of the peripheral vessels, and diseases of the urogenital system.

Phosphodiesterases (PDEs) play an important role in the regulation of the intracellular cGMP and cAMP level. Amongst the phosphodiesterase isoenzyme groups PDE I to PDE V which have been described to date [Nomenclature of Beavo and Reifsnyder (cf. Beavo, J. A. and Reifsnyder, D. H.: Trends in Pharmacol. Sci 11, 150–155 (1990)], the Ca-calmodulin-activated PDE I, the cGMP-stimulateable PDE II and the cGMP-specific PDE V are essentially responsible for the cGMP metabolism. Due to the different distribution of these cGMP-metabolizing PDEs in the tissue, selective inhibitors should, depending on the distribution in the tissue of the isoenzyme in question, increase the c-GMP levels in the tissue in question. This may lead to a specific antiaggregatory, antispastic, vasodilatory and/or antiarrhythmic action.

Moreover, U.S. Pat. No. 5,294,612, U.S. Pat. No. 4,211,731, U.S. Pat. No. 3,211,732, WO 96/28448 and WO 96/28429 disclose 6-heterocyclyl-pyrazolo[3,4-d]pyrimidin-3-one and 6-substituted pyrazolo[3,4-d]pyrimidin-4-ones, which can be employed for hypertension, angina and heart diseases.

The present invention now relates to 1,5-dihydro-pyrazolo[3,4-d]-pyrimidinone derivatives of the general formula (I)

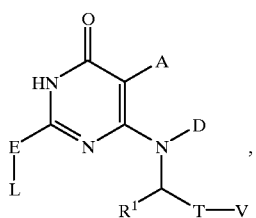

(I)

in which

A and D together represent a radical of the formula

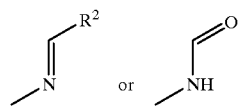

where
R² represents aryl which has 6 to 10 carbon atoms and which is optionally up to trisubstituted by identical or different substituents from the series consisting of nitro, cyano, hxdroxyl, trifluoromethyl, halogen, carboxyl, or by straight-chain or branched acyl, alkoxy or alkoxycarbonyl, each of which has up to 6 carbon atoms or
hydrogen, trifluoromethyl, cyano, carboxyl, or straight-chain or branched alkoxy or alkoxycarbonyl, each of which has up to 8 carbon atoms, or straight-chain or branched alkyl which has up to 8 carbon atoms and which is optionally substituted by hydroxyl, R¹ represents straight-chain or branched acyl having up to 4 carbon atoms, or
represents straight-chain or branched alkyl having up to 10 carbon atoms, optionally substituted by hydroxyl, azido or by a group of the formula —NR³R⁴ or —OSO₂R⁵
where
R³ and R⁴ are identical or different and
represent hydrogen or straight-chain or branched alkyl having up to 6 carbon atoms, or
R³ and R⁴ together with the nitrogen atom form a 5 or 6-membered saturated heterocycle which can optionally contain a further hetero atom selected from the series consisting of S or O or a radical —NR⁶
where
R⁶ represent hydrogen or straight-chain or branched alkyl is up to 4 carbon atoms
and
R⁵ represents phenyl or straight-chain or branched alkyl having up to 5 carbon atoms,
E represents a straight-chain or branched alkylene or alkenylene chain, each of which has up to 6 carbon atoms which are optionally substituted by hydroxyl, or represents the C=O group,
L and V are identical or different and represent aryl having 6 to 10 carbon atoms or a 5- to 7-membered aromatic, optionally benzo-fused, heterocycle which has up to 3 hetero atoms from the series consisting of S, N and/or O which are optionally up to trisubstituted by identical or different substituents from the series consisting of halogen, hydroxyl, nitro, trifluoromethyl, carboxyl, straight-chain or branched alkyl, alkoxy or alkoxycarbonyl, each of which has up to 6 carbon atoms, or by a group of the formula —(W)ₐ—NR⁷R⁸
where
a is a number 0 or 1,
W is a radical of the formula —CO or —SO₂,
R⁷ and R⁸ are identical or different and have the abovementioned meaning of R³ and R⁴,
and/or the cycles are optionally substituted by aryl having 6 to 10 carbon atoms or by a 5- to 7-membered aromatic, optionally benzo-fused, heterocycle having up to 3 hetero atoms from the series consisting of S, N and/or O, which, in turn, are optionally up to disubstituted by identical or different substituents from the series consisting of halogen, hydroxyl, nitro, carboxyl, trifluoromethyl or by straight-chain or branched alkyl, alkox or alkoxycarbonyl, each of which has up to 5 carbon atoms, or by a group of the formula —(W')ᵇ—NR⁹R¹⁰
where
b has the abovementioned meaning of a and is identical to this meaning or different from it,
R⁹ and R¹⁰ have the abovementioned meaning of R³ and R⁴ and are identical to this meaning or different from it,
W' has the abovementioned meaning of W and is identical to this meaning or different from it,
or L represents a radical of the formula

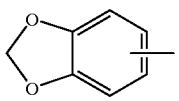

or

V represents methyl,

T represents a radical of the formula —CH$_2$—X—Y— where

X represents a bond or an oxygen or sulphur atom or the —NH-group,

Y represents a straight-chain or branched alkylene chain having up to 9 carbon atoms, and the tautomers and salts of these.

The substances according to the invention may also be present as salts. Preferred within the scope of the invention are physiologically acceptable salts.

Physiologically acceptable salts can be salts of the compounds according to the invention with inorganic or organic acids. Preferred are salts with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid or naphthaline disulphonic acid.

Equally, physiologically acceptable salts may be metal salts or ammonium salts of the compounds according to the invention which have a free carboxyl group. Especially preferred examples are sodium, potassium, magnesium or calcium salts, and also ammonium salts which are derived from ammonia, or organic amines such as, for example, ethylamine, di- or triethylamine, di- or triethanolamine, dicyclohexylamine, dimethylaminoethanol, arginine, lysine, ethylenediamine or 2-phenylethylamine.

The compounds of the general formula (I) according to the invention can occur in various stereochemical forms which relate to each other either like image and mirror image (enantiomers) or which do not relate to each other like image and mirror image (diastereomers). The invention relates not only to the antipodes, but also to the racemic forms and the diastereomer mixtures. The racemic forms and the diastereomers can be separated in a known manner to give the stereoisomerically uniform constituents.

Within the scope of the invention, heterocycle generally represents a saturated or unsaturated 5- to 7-membered, preferably 5- to 6-membered, heterocycle which can contain up to 3 hetero atoms from the series consisting of S, N and/or O. Examples which may be mentioned are: pyridyl, thienyl, indonyl furyl, pyrrolyl, thiazolyl, oxazolyl, imidazolyl, morpholinyl or piperidyl. Pyridyl, thienyl, indolyl and furyl are preferred.

Preferred compounds of the general formula (I) are those in which

A and D together represent a radical of the formula

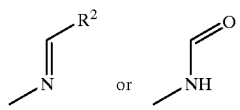

where

R$^2$ represents phenyl which is optionally up to disubstituted by identical or different substituents from the series consisting of nitro, cyano, hxdroxyl, trifluoromethyl, fluorine, chlorine, bromine, carboxyl or by straight-chain or branched acyl, alkoxy or alkoxycarbonyl, each of which has up to 5 carbon atoms, or hydrogen, trifluoromethyl, cyano, carboxyl, straight-chain or branched alkoxy or alkoxycarbonyl, each of which has up to 6 carbon atoms, or straight-chain or branched alkyl which has up to 6 carbon atoms and which is optionally substituted by hydroxyl, R$^1$ represents straight-chain or branched acyl having up to 6 carbon atoms, or straight-chain or branched alkyl which has up to 8 carbon atoms and which is optionally substituted by hydroxyl, azido or by a group of the formula —NR$^3$R$^4$ or O—SO$_2$—R$^5$ in which R$^3$ and R$^4$ are identical or different and represent hydrogen or straight-chain or branched alkyl having up to 5 carbon atoms, or R$^3$ and R$^4$ together with the nitrogen atom form a morpholinyl-piperidinyl or piperazinyl ring, the latter optionally being substituted via the nitrogen function by straight-chain or branched alkyl having up to 3 carbon atoms, and R$^5$ represents phenyl or straight-chain or branched alkyl having up to 4 carbon atoms, E represents a straight-chain or branched alkylene or alkenylene chain, each of which has up to 5 carbon atoms and each of which is optionally substituted by hydroxyl, or represents the C=O group, L and V are identical or different and represent phenyl, naphthyl, pyridyl, thienyl, indolyl or furyl, each of which is up to trisubstituted by identical or different substituents from the series consisting of fluorine, chlorine, bromine, trifluoromethyl, hydroxyl, nitro, carboxyl, straight-chain or branched alkyl, alkoxy or alkoxycarbonyl, each of which has up to 5 carbon atoms, or by a group of the formula —(W)$_a$NR$^7$R$^8$ in which a represents a number 0 or 1, W represents a radical of the formula —CO or —SO$_2$, R$^7$ and R$^8$ are identical or different and have the abovementioned meaning of R$^3$ and R$^4$, and/or the cycles are optionally substituted by naphthyl, phenyl, pyridyl, indolyl, thienyl or furyl, optionally by phenyl, naphthyl, pyridyl, thienyl, furyl, pynyl or pyrimidyl, which, in turn, are optionally substituted by fluorine, chlorine, bromine, hydroxyl, nitro, carboxyl, trifluoromethyl or straight-chain or branched alkyl, alkoxy or alkoxycarbonyl, each of which has up to 3 carbon atoms, or by a group of the formula —(W')$_b$NR$^9$R$^{10}$ in which b has the abovementioned meaning of a and is identical to this meaning or different from it, W' has the abovementioned meaning of W and is identical to this meaning or different from it, R$^9$ and R$^{10}$ have the abovementioned meaning of R$^3$ and R$^4$, or L represents a radical of the formula

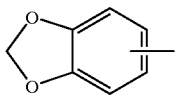

or

V represents methyl,

T represents a radical of the formula —CH$_2$—X—Y— in which
X represents a bond or an oxygen or sulphur atom or the —NH-group,
Y represents a straight-chain or branched alkylene chain having up to 8 carbon atoms, and the tautomers and salts of these.

Especially preferred are compounds of the general formula (I)
in which
A and D together represent a radical of the formula

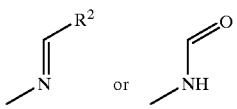

in which
R$^2$ represents phenyl which is optionally up to disubstituted by identical or different substituents from the series consisting of nitro, cyano, hxdroxyl, trifluoromethyl, fluorine, chlorine, bromine, carboxyl or by straight-chain or branched acyl, akoxy or alkoxycarbonyl, each of which has up to 4 carbon atoms, or
represents hydrogen, trifluoromethyl, cyano, carboxyl, straight-chain or branched alkoxy or alkoxycarbonyl, each of which has up to carbon atoms, or straight-chain or branched alkyl which has up to carbon atoms and which is optionally substituted by hydroxyl,
R$^1$ represents straight-chain or branched acyl having up to 5 carbon atoms, or
represents straight-chain or branched alkyl which has up to 6 carbon atoms and which is optionally substituted by hydroxyl, azido or by a group of the formula —NR$^3$R$^4$ or O—SO$_2$R$^5$
in which
R$^3$ and R$^4$ are identical or different and represent hydrogen or straight-chain or branched alkyl having up to 4 carbon atoms, or
R$^3$ and R$^4$ together with the nitrogen atom form a morpholinyl, piperdinyl or piperazinyl ring, the latter optionally being methyl-substituted via the nitrogen function,
and
R$^5$ represents phenyl or straight-chain or branched alkyl having up to 3 carbon atoms,
E represents a straight-chain or branched alkylene or alkenylene chain, each of which has up to 5 carbon atoms which are optionally substituted by hydroxyl, or represents the C=O group,
L and V are identical or different and represent phenyl, naphthyl, furyl, thienyl, indolyl or pyridyl, each of which is optionally up to trisubstituted by identical or different substituents from the series consisting of fluorine, chlorine, bromine, hydroxyl, nitro, carboxyl, straight-chain or branched alkyl, alkoxy or alkoxycarbonyl, each of which has up to 4 carbon atoms, or by a group of the formula —(W)$_a$NR$^7$R$^8$
in which
a represents a number 0 or 1,
W represents a radical of the formula —CO or —SO$_2$,
R$^7$ and R$^8$ are identical or different and have the abovementioned meaning of R$^3$ and R$^4$,
and/or the cycles are optionally substituted by phenyl, pyridyl, thienyl or furyl, which, in turn, are optionally substituted by fluorine, chlorine, bromine, hydroxyl, nitro, carboxyl, trifluoromethyl or by straight-chain or branched alkyl, alkoxy or alkoxycarbonyl, each of which has up to 3 carbon atoms, or by a group of the formula —(W')$_b$NR$^9$R$^{10}$
in which
b has the abovementioned meaning of a and is identical to this meaning or different from it,
W' has the abovementioned meaning of W and is identical to this meaning or different from it,
R$^9$ and R$^{10}$ have the abovementioned meaning of R$^3$ and R$^4$,
or
L represents a radical of the formula

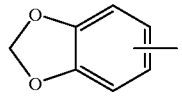

or
V represents methyl,
T represents a radical of the formula —CH$_2$—X—Y— in which
X represents a bond or an oxygen or sulphur atom or the —NH-group,
Y represents a straight-chain or branched alkylene chain having up to 6 carbon atoms,
and the tautomers and salts of these.

Very especially preferred are compounds of the general formula (I) according to the invention
in which
A and D together represent a radical of the formula

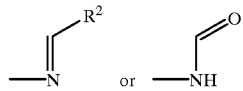

in which
R$^2$ represents straight-chain or branched alkyl or alkoxy, which has up to 3 carbon atoms,
R represents a straight-chain or branched alkyl having up to 3 carbon atoms or
a radical of the formula

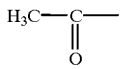

E represents a straight-chain or branched alkylene chain which has up to 3 carbon atoms and which is optionally substituted by hydroxyl,
T represents a radical of the formula —CH$_2$—X—Y— in which

X represents a bond and

Y represents a straight-chain or branched alkylene chain having up to 5 carbon atoms, V represents methyl or phenyl, L represents a radical of the formula

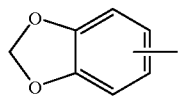

or phenyl which is optionally up to trisubstituted by identical or different substituents from the series consisting of fluorine, chlorine, bromine, pyridyl, straight-chain or branched alkyl or alkoxycarbonyl, each of which has up to 3 carbon atoms, amino or by a radical of the formula —$SO_2$—$NHCH_3$

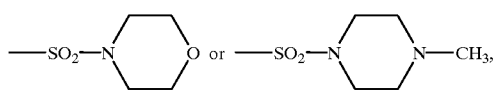

and/or can be substituted by phenyl or by nitro-substituted phenyl, and the tautomers and salts of these.

Moreover, a process for the preparation of the compounds of the general formula (I) according to the invention has been found, characterized in that

[A] in the event that A and D together represent the radical of the formula

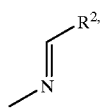

compounds of the general formula (II)

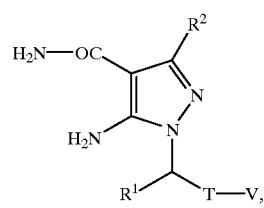

(II)

in which $R^1$, $R^2$, T and V have the abovementioned meaning are firstly converted into the compounds of the general formula (IV)

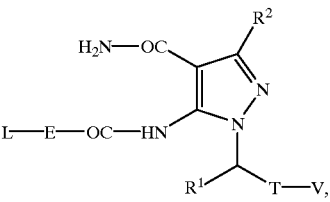

(IV)

in which

E, L, T, V, $R^1$ and $R^2$ have the abovementioned meaning by reacting them, in inert solvents and in the presence of a base, with compounds of the general formula (III)

$$L—E—CO—Cl \quad (III)$$

in which

E and L have the abovementioned meaning
and subsequently cyclizing the product with bases,
or

[B] compounds of the general formula (II) are reacted, with direct cyclization, with compounds of the general formula (IIIa)

$$L—E—CO_2—R^{11} \quad (IIIa)$$

in which

E and L have the abovementioned meaning
and
$R^{11}$ represents methyl or ethyl,
and, in a second step, the product is cyclized in inert solvents and in the presence of a base,
or

[C] compounds of the general formula (V)

(V)

in which $R^1$, $R^2$, T and V have the abovementioned meaning are first reacted with compounds of the general formula (III) in inert solvents and in the presence of a base to give the compounds of the general formula (VI)

(VI)

in which $R^1$, $R^2$, E, L, T and V have the abovementioned meaning, and, in a 2nd step, cyclizing the product in inert solvents and in the presence of a base and of an oxidant, or

[D] in the event that A and D together represent the radical of the formula

the corresponding compounds of the general formula (I) in which $R^2$ represents methoxy is reacted in the system sodium iodide/trimethylchlorosilane in inert solvents, and, if appropriate, the substituents mentioned under $R^1$ are introduced or derivatized by subsequent reactions such as acylation, oxidation, substitution and/or reductions, and, equally, the substituents mentioned above under L and V are introduced and/or varied by customary methods.

The process according to the invention can be illustrated by way of example with reference to the following formula scheme:

[A]

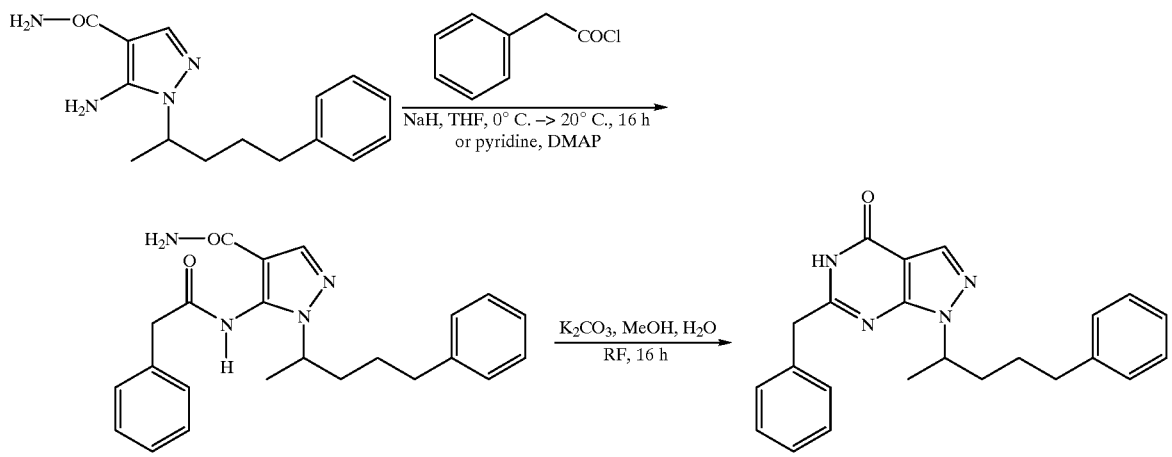

[B]

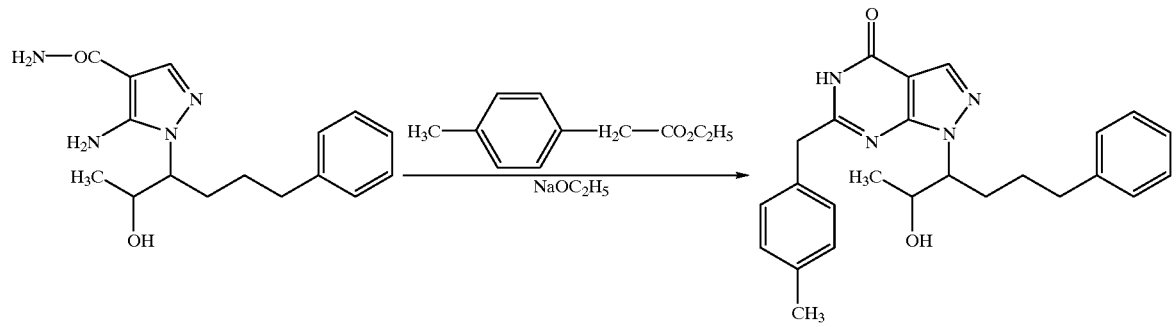

[C]

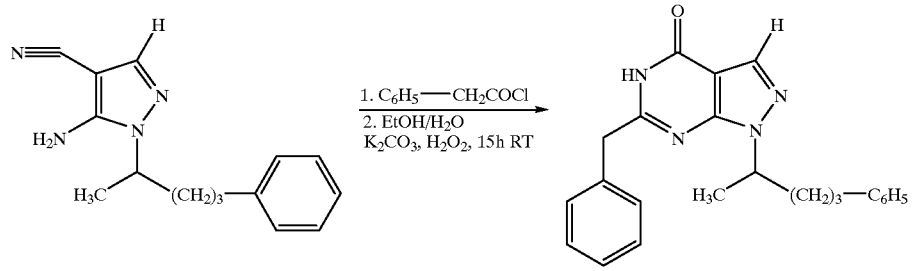

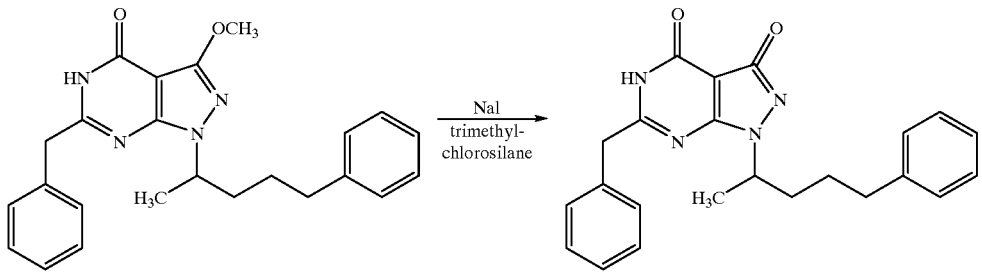

Suitable solvents for the first step of process [A] and process [C] are inert organic solvents which do not change under the reaction conditions. These preferably include ethers such as, for example, diethyl ether, dioxane, tetrahydrofuran or glycol dimethyl ether or toluene, hexamethylphosphoric triamide and pyridine. Naturally, solvent mixtures may be used. Especially preferred are tetrahydrofuran, toluene or pyridine.

Suitable bases are, in general, alkali metal hydrides or alkali metal alkoxides such as, for example, sodium hydride or potassium tert-butoxide, or cyclic amines such as, for example, piperidine, pyridine, dimethylaminopyridine or $C_1$–$C_4$-alkylamines such as, for example, triethylamine. Preferred are sodium hydride, pyridine and/or dimethylaminopyridine.

In general, the base is employed in an amount of 1 mol to 4 mol, preferably 1.2 mol to 3 mol, in each case per mole of the compounds of the general formula (II) and (V).

In general, the reaction temperature can be varied within a substantial range. In general, the process is carried out in a range of –20° C. to 200° C., preferably 0° C. to 100° C.

In one variant, the reaction is carried out in pyridine to which a catalytic amount of DMAP is added. If appropriate, toluene may also be added.

Suitable solvents for the cyclization reaction are the customary organic solvents. These preferably include alcohols such as methanol, ethanol, propanol, isopropanol, butanol or t-butanol, or ethers such as tetrahydrofuran or dioxane, or dimethylformamide or dimethyl sulphoxide. Alcohols such as methanol, ethanol, propanol, isopropanol or t-butanol are especially preferably used. Mixtures of the above solvents may also be employed.

Bases which are suitable for the cyclization reaction are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate, potassium carbonate or sodium hydrogen carbonate, or alkali metal alkoxides such as sodium methoxide, sodium ethoxide, potassium methoxide, potassium ethoxide or potassium tert-butoxide. Potassium carbonate, sodium hydroxide and potassium tert-butoxide are especially preferred.

When carrying out the cyclization reaction, the base is generally employed in an amount of 2 to 6 mol, preferably 3 to 5 mol, per mol of the compounds of the formula (IV).

Suitable oxidants for the cyclization reaction are, for example, hydrogen peroxide or sodium borate. Hydrogen peroxide is preferred.

In general, the cyclization reaction is carried out in a temperature range between 0° C. and 160° C., preferably at the boiling point of the solvent in question.

In general, the cyclization reaction is carried out under atmospheric pressure. However, it is also possible to carry out the process under superatmospheric or subatmospheric pressure (for example in a range between 0.5 to 5 bar).

Suitable solvents for process [B] are the abovementioned alcohols, ethanol being preferred.

Suitable bases for process [B] are alkoxides such as, for example, sodium methoxide, sodium ethoxide, sodium isopropoxide or potassium tert-butoxide. Sodium ethoxide is preferred.

The base is employed in an amount of 2 to 8 mol, preferably 3 mol to 6 mol, in each case per mole of the compounds of the general formula (II).

The preferred solvent for process [D] is acetonitrile. In general, the process is carried out under reflux conditions and under atmospheric pressure.

Starting from the corresponding free hydroxyl compounds, the reaction with alkylsulphonyl chlorides is carried out in one of the abovementioned solvents and one of the bases, preferably with dichloromethane and triethylamine, in a temperature range between –20° C. to +20° C., preferably 0C and atmospheric pressure.

The azide radical is generally introduced by reacting the corresponding alkylsulphonyloxy-substituted compounds with sodium azide in one of the abovementioned solvents, preferably dimethylformamide, in a temperature range between 50° C. and +120° C., preferably 100° C. and atmospheric pressure.

Starting from the corresponding hydroxyl compounds, the ketones are prepared by known methods (Swern oxidation or Collins oxidation).

The substituents on the aromatic rings are varied by known methods.

The enantiomerically pure compounds can be obtained by customary methods, for example by chromatography of the racemic compounds of the general formula (I) on chiral phases, or by using chiral starting compounds.

The compounds of the general formula (V) are new and can be prepared, for example, by reacting—in the event that $R^2 \ne OCH_3$—malononsitrile with compounds of the general formula (VII)

$$R^2C(OC_2H_5)_3 \qquad (VII)$$

in which $R^2$ has the abovementioned meaning and, in a second step, with compounds of the general formula (VIII)

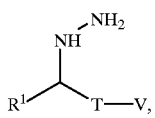

(VIII)

in which

R[1], T and V have the abovementioned meaning in inert solvents, and—in the event that R[2]=OCH$_3$—reacting the compounds of the general formula (VIII) directly with 1,1-dimethoxy-2,2-dicyano-ethylene.

Suitable solvents for the individual process steps are the customary organic solvents which do not change under the reaction conditions. These preferably include alcohols such as methanol, ethanol, propanol or isopropanol, or ethers such as diethyl ether, dioxane, tetrahydrofuran, glycol dimethyl ether, or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetate, dimethylformamide, hexamethylphosphoric triamide, acetonitrile, acetone, dimethoxyethane or pyridine. Mixtures of the above solvents may also be used. Especially preferred are acetonitrile in the event that R$^2 \neq$ OCH$_3$ and pyridine in the event that R$^2$=OCH$_3$.

In general, the process according to the invention is carried out in a temperature range between 0° C. and +180° C., preferably between +30° C. and +150° C.

These process steps according to the invention are generally carried out at atmospheric pressure. However, the process may also be carried out at superatmospheric pressure or subatmospheric pressure (for example in a range between 0.5 and 5 bar).

Most of the compounds of the general formula (IV) and (VI) are new and can be prepared as described above.

The compounds of the general formula (III), (IIa), (VII) and (VIII) are known per se or can be prepared by customary methods.

The compounds of the general formula (II) are new and can be prepared by reacting the compounds of the general formula (V) with one of the abovementioned oxidants, preferably hydrogen peroxide, in the presence of ammonia or dichloromethane, or with a phase transfer catalyst.

Some of the compounds of the general formula (V) are known or new or can be prepared by customary methods.

The compounds of the general formula (I) according to the invention have a valuable pharmacological spectrum of action which could not have been foreseen.

They inhibit either one or more of the c-GMP-metabolizing phosphodiesterases (PDE I, PDE II and PDE V). This leads to a differentiated increase in c-GMP. An increased c-GMP level can lead to an antithrombotic, vasodilatory and/or antiarrhythmic action. The differentiating action is determined, inter alia, by the distribution of the isoenzymes in the tissue.

Moreover, the compounds according to the invention promote the action of substances such as, for example, EDRF (endothelium derived relaxing factor) and ANP (atrial natriuretic peptide) which increase the cGMP level.

They can therefore be used in medicaments for treating cardiovascular diseases such as, for example, for treating hypertension, neuronal hypertension, stable and unstable angina, diseases of the peripheral and cardial blood vessels, of arrythmias, for treating thromboembolic diseases and ischaemias such as myocardial infarction, stroke, transistory and ischaemic attacks, angina pectoris, peripheral circulation disorders, prevention of restenoses after thrombolytic therapy, percutaneous transluminal angioplasty (PTA), percutaneous transluminal coronary angioplasties (PTCA) and bypass. The relaxing effect on the smooth muscles makes them suitable for the treatment of diseases of the urogenital system such as prostatic hypertrophy, impotence and incontinence. Moreover, they can also be of importance for cerebral vascular diseases.

Phosphodiesterase (PDE) Activity

The c-GMP-stimulatable PDE II, the c-GMP-inhibitable PDE III and the cAMP-specific PDE IV were isolated either from porcine or bovine heart myocard. The Ca$^{2+}$-calmodulin-stimulatable PDE I was isolated from porcine aorta, porcine brain or, preferably, bovine aorta. The c-GMP-specific PDE V was obtained from porcine small intestine, porcine aorta, human platelets and, preferably, bovine aorta. They were purified by anion exchange chromatography on MonoQ® Pharmacia following essentially the method of M. Hoey and Miles D. Houslay, Biochemical Pharmacology, Vol. 40, 193–202 (1990) and C. Lugman et al. Biochemical Pharmacology Vol. 35 1743–1751 (1986).

The enzyme activity is determined in a test batch of 100 µl in 20 mM Tris/HCl buffer pH 7.5 which comprises 5 mM MgCl$_2$, 0.1 mg/ml bovine serum albumin and either 800 Bq $^3$HcAMP or $^3$HcGMP. The end concentration of the corresponding nucleotide is 10$^{-6}$ mol/l. The reaction is started by adding the enzyme, and the quantity of enzyme is such that approx. 50% of the substrate are converted during the incubation time of 30 minutes. To test the cGMP-stimulatable PDE II, $^3$HcAMP is used as substrate, 10$^{-6}$ mol/l unlabelled cGMP are added to the batch. To test the Ca-calmodulin-dependent PDE I, 1 µM CaCl$_2$ and 0.1 µM calmodulin are also added to the reaction batch. The reaction is stopped by adding 100 µl of acetonitrile which contains 1 mM cAMP and 1 mM AMP. 100 µl of the reaction batch are separated by HPLC and the cleavage products are quantified on-line using a flow scintillation counter. The substance concentration at which the reaction rate is reduced by 50% is measured. Also used for testing were the "Phosphodiesterase [$^3$H] cAMP-SPA enzyme assay" and the "Phosphodiesterase [$^3$H]cGMP-SPA enzyme assay" by Amersham Life Science. The test was performed following the manufacturer's protocol. To determine the PDE2 activity, the [$^3$H] cAMP SPA assay was used, 10$^{-6}$ M cGMP being added to the reaction batch for activating the enzyme. To measure PDE1, 10$^{-7}$ M calmodulin and 1 µM CaCl$_2$ were added to the reaction batch. PDE5 was measured using the [$^3$H] cGMP SPA assay.

| | Phosphodiesterase inhibition in vitro | | |
|---|---|---|---|
| Example No. | PDE I IC$_{50}$ [nM] | PDE II IC$_{50}$ [nM] | PDE V IC$_{50}$ [nM] |
| 9 | 300 | 300 | 300 |
| 10 | 300 | 500 | 50 |
| 11 | >10,000 | 100 | 50 |
| 32 | 500 | 300 | 300 |
| 33 | 500 | 500 | 800 |

The compounds were tested for antihypertensive activity on the anaesthetized pig.

The erection-triggering effect was measured on the anaesthetized rabbit (C. G. Stief et al., World Journal Urology 1990, pp. 233–236).

The substances were applied directly into the corpus cavernosum, intraduodenally, rectally, orally, transdermally or intravenously at dosages from 0.03 to 10 mg/kg.

The new active compound can be converted in a known manner into the customary formulations such as tablets, coated tablets, pills, granules, aerosols, syrups, emulsions, suspensions and solutions, using inert non-toxic pharmaceutically suitable excipients or solvents. The therapeutically active compound should be present in each case in a concentration of approximately 0.5 to 90% by weight of the total mixture, i.e. in amounts which suffice to attain the dosage range indicated.

For example, the formulations are prepared by extending the active compounds with solvents and/or excipients, if appropriate using emulsifiers and/or dispersants, it being possible, if appropriate, for organic solvents to be used as auxiliary solvents if, for example, water is used as the diluent.

Application is effected in the customary manner, preferably orally, transdermally or parenterally, in particular perlingually or intravenously.

To achieve effective results, it has generally proved advantageous to administer, with intravenous application, amounts of approximately 0.01 to 10 mg/kg, preferably approximately 0.1 to 10 mg/kg bodyweight.

Nevertheless, it may be required to deviate from the abovementioned amounts, depending on the bodyweight or the route of application, the individual behaviour towards the medicament, the nature of its formulation and the point in time or interval at which it is administered. Thus, it may suffice in some cases to make do with less than the abovementioned minimal amount, while the abovementioned upper limit will have to be exceeded in other cases. If larger amounts are administered, it may be recommendable to distribute them over the day in the form of several individual doses.

Starting Compound

EXAMPLE I tert-Butyl N'-(1-methyl-4-phenyl-butylidene)-hydrazine-carboxylate

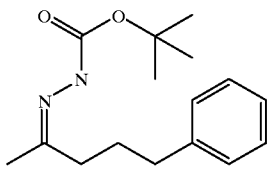

10.2 g (63 mmol) of 5-phenylpentan-2-one and 8.44 g (62 mmol) of tert-butylcarbazate are dissolved in 100 ml of heptane, and stirred for 20 minutes at room temperature and for 60 minutes under reflux. The mixture is crystallized for 5 hours at 4° C., and the crystals are filtered off with suction, washed with pentane and dried.

Yield: 14.6 g (96%).

$R_f$=0.15 (PE/EA=9:1)

EXAMPLE II (1-Methyl-4-phenyl-butyl)-hydrazine

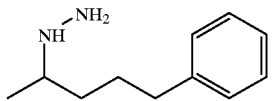

10.53 g (38 mmol) of tert-butyl N'-(1-methyl-4-phenyl-butylidene)-hydrazine-carboxylate are dissolved in 30 ml of THF and 40 ml of methanol, 2.77 g (44 mmol) of $NaBH_3CN$ are added, and the mixture is stirred for 60 minutes at room temperature. After 27.2 ml of 6N HCl have been added dropwise, the mixture is refluxed for 60 minutes. It is neutralized with 6N sodium hydroxide solution, the non-aqueous solvents are distilled off, and the aqueous phase is extracted three times with ethyl acetate. The organic phase is dried over $Na_2SO_4$ and the solvent is removed in vacuo.

Yield: 6.78 g (99%) of a yellow oil.

$R_f$=0.10 (PE/EA=5:1)

EXAMPLE III

5-Amino-1-(1-methyl-4-phenyl-butyl)-1H-pyrazol-4-carbonitrile

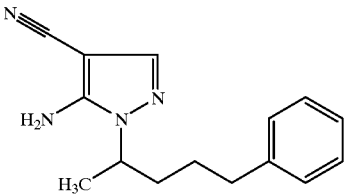

7.70 g (43 mmol) of (1-methyl-4-phenyl-butyl)-hydrazine 10 ml of methanol are added to 5.28 g (43 mmol) of ethoxymethylenemalononitrile in 50 ml of methanol, and the mixture is stirred for 15 minutes at room temperature. The mixture is refluxed for 2 hours and the solvent is then removed in vacuo. The residue is taken up in 100 ml of $CH_2Cl_2$, the organic phase is extracted with saturated aqueous $NaHCO_3$ solution, dried over $Na_2SO_4$ and a spatula-tip full of active charcoal, and the solvent is removed in vacuo.

Yield: 9.70 g (88%) of a red oil.

$R_f$=0.15 (PE/EA=2:1)

EXAMPLE IV

5-Amino-1-(1-methyl-4-phenyl-butyl)-1H-pyrazole-4-carboxamide

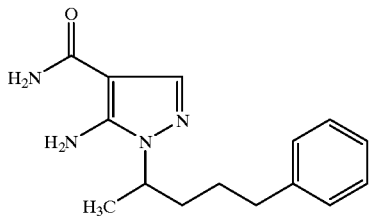

512 mg (2.02 mmol) of 5-amino-1-(1-methyl-4-phenyl-butyl)-1H-pyrazole-4-carbonitrile are stirred for 3 hours at room temperature with 25 ml of concentrated aqueous $NH_3$, 20 ml of ethanol and 5 ml of 30% strength $H_2O_2$. The non-aqueous solvent is removed in vacuo, and the solid which has precipitated is filtered off with suction and dried.

Yield: 408 mg (75%) of a white solid.

M.p.: 128° C.

EXAMPLE V 2-(1-Ethoxy-propylidene)-malononitrile

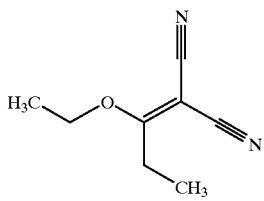

16.41 g (249 mmol) of malononitrile and 43.8 g (249 mmol) of triethyl orthopropionate are refluxed for 4.5 hours. The reaction mixture is cooled to room temperature and distilled in vacuo.

B.p.: 90° C. (3 mbar)

Yield: 28.4 g (75%)

EXAMPLE VI 2-(1-Ethoxy-ethylidene)-malononitrile

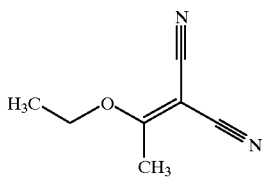

8.26 g (125 mmol) of malononitrile and 20.25 g (125 mmol) of triethyl orthoacetate are refluxed for hours. After cooling, the mixture is dried in vacuo.

Yield: 16.0 g (quantitative)

EXAMPLE VII

5-Amino-3-ethyl-1-(1-methyl-4-phenyl-butyl)-1-H-pyrazole-4-carbonitrile

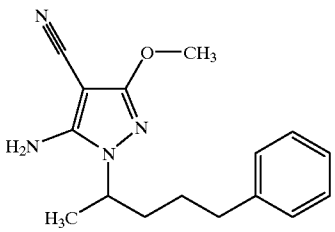

5 g (28 mmol) of (1-methyl-4-phenyl-butyl)-hydrazine and 4.17 g (28 mmol) of 2-(1-ethoxypropylidene)-malononitrile are refluxed for 2.25 hours in 150 ml of methanol. The solvent is removed in vacuo, the residue is taken up in 100 ml of $CH_2Cl_2$, the mixture is extracted with 0.1N HCl and saturated aqueous $NaHCO_3$ solution and dried over $Na_2SO_4$, and the solvent is removed in vacuo.

Yield: 7.2 g (99%) of a red oil.

$R_f$=0.15 (PE/EA=2:1).

EXAMPLE VIII

2-Hydroxy-6-phenyl-hexane-3-one

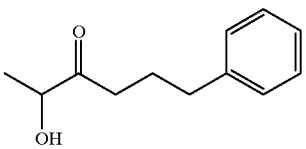

7.3 (55 mmol) of trimethylsilyl cyanide are cooled to 0° C. under argon, and 2 drops of $BF_3.OET_2$ and 3.1 ml (55 mmol) of acetaldehyde are added successively. The mixture is stirred for 1.5 h at room temperature, and the resultant cyanohydrin is dissolved in 10 ml of ether. 1 ml (6.6 mmol) of 3-phenyl-1-propyl bromide is added to 1.3 g (55 mmol) of magnesium in 4 ml of ether under argon. After the spontaneous reaction has subsided, a further 7.4 ml (48.7 mmol) of 3-phenyl-1-propyl bromide, dissolved in 10 ml of ether are added dropwise at such a rate that gentle reflux is maintained. After the addition has ended, the mixture is refluxed for 30 minutes and then cooled to 0° C. The cyanohydrin solution is added dropwise at 0° C. and the reaction mixture is stirred for 15 hours at room temperature. The reaction mixture is diluted with 100 ml of ether, poured into a mixture of 300 g of ice and 15 ml of concentrated $H_2SO_4$ and stirred for 3 hours at room temperature. The ether phase is extracted three times with 10% strength HCl and once with saturated sodium chloride solution and dried over $Na_2SO_4$, and the solvent is removed in vacuo.

Yield: 7.15 g (68%) of colourless oil.

$R_f$: 0.12 (PE/EA=9:1)

EXAMPLE IX tert-Butyl N'-(1-methyl-4-phenyl-butylidene)-hydrazine-carboxylate

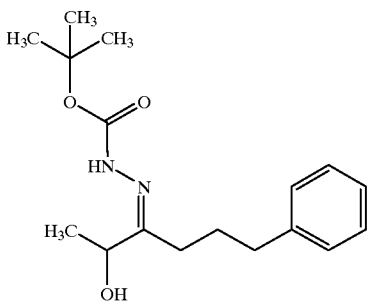

8.1 g (42 mmol) of 2-hydroxy-6-phenylhexan-3-one and 5.68 g of tert-butyl carbazate (43 mmol) are dissolved in 70 ml of heptane and 35 ml of THF and stirred for 30 minutes at room temperature and for 1.5 hours under reflux conditions. The solvent is removed in vacuo.

Yield: 12.81 g (99%) of yellow oil.

$R_f$:0.10 (PE/EA=9:1).

EXAMPLE X

5-Amino-1-[1-(1-hydroxy-ethyl)-4-phenyl-butyl]-1H-pyrazole-4-carbonitrile

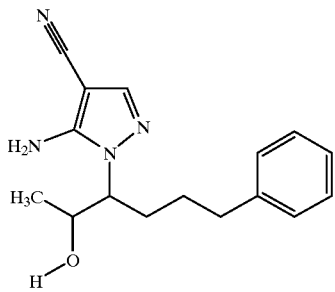

12.79 g (42 mmol) of tert-butyl N'-(1-methyl-4-phenyl-butylidene)-hydrazinecarboxylate are dissolved in 30 ml of THF and 40 ml of methanol, 6.08 g (97 mmol) of NaBH$_3$CN are added, and the mixture is stirred for 60 minutes at room temperature. After 35 ml of 6N HCl have been added dropwise, the mixture is refluxed for 60 minutes. It is neutralized with 6N sodium hydroxide solution and extracted three times with CH$_2$Cl$_2$. The organic phase is dried over Na$_2$SO$_4$ and the solvent is removed in vacuo. This gives 7.38 g of a pale yellow oil. 6.5 g of this oil are first stirred with 3.93 g (32 mmol) of ethoxymethylenemalononitrile in 200 ml of methanol for one hour at room temperature and then refluxed for 2 hours. After cooling, the solvent is removed in vacuo. Purification by chromatography (PE/EA=2:1) gives 5.28 g of a colourless oil.

$R_f$: 0.10 (PE/EA=2:1).

EXAMPLE XI

5-Amino-1-[1-(1-hydroxy-ethyl)-4-phenyl-butyl]-1H-pyrazole-4-carboxamide

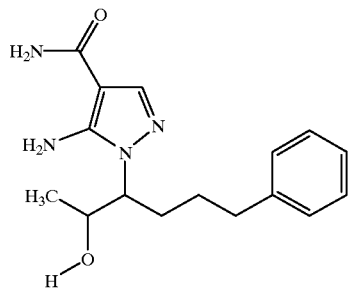

3.9 g (13.7 mmol) of 5-amino-1-[1-(1-hydroxy-ethyl)-4-phenyl-butyl]-1H-pyrazole-4-carbonitrile and 960 mg of tetrabutylammonium hydrogen sulphate are dissolved in 28 ml of CH$_2$Cl$_2$, 5.5 ml of 5M NaOH and 7 ml of 30% strength H$_2$O$_2$ are added, and the mixture is stirred for 4 hours at room temperature. The phases are separated, the organic phase is extracted twice with water, the organic phase is dried over Na$_2$SO$_4$, and the solvent is removed in vacuo.

Yield: 3.8 g (92%)

M.p.:116° C. (PE/EA)

EXAMPLE XII

5-Amino-1-[1-(1-hydroxy-ethyl)-4-phenyl-butyl]-3-methyl-1H-pyrazole-4-carbonitrile

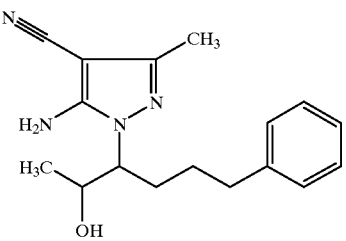

12.79 g (42 mmol) of tert-butyl N'-(1-methyl-4-phenyl-butylidene)-hydrazinecarboxylate are dissolved in 30 ml of THF and 40 ml of methanol, 6.08 g (97 mmol) of NaBH$_3$CN are added, and the mixture is stirred for 60 minutes at room temperature. After 35 ml of 6N HCl have been added dropwise, the mixture is refluxed for 60 minutes. It is neutralized with 6N sodium hydroxide solution and extracted three times with CH$_2$Cl$_2$. The organic phase is dried over Na$_2$SO$_4$ and the solvent is removed in vacuo. This gives 7.38 g of a pale yellow oil. 2.64 g of this oil (11.3 mmol) and 1.4 g of 2-(1-ethoxy-ethylidene)-malononitrile (11.3 mmol) are refluxed for 2 hours in 20 ml of methanol. The solvent is removed in vacuo.

3.73 g of a red oil.

$R_f$: 0.11 (PE/EA=2:1)

EXAMPLE XIII

5-Amino-1-[1-(1-hydroxy-ethyl)-4-phenyl-butyl]-3-methyl-1H-pyrazole-4-carboxamide

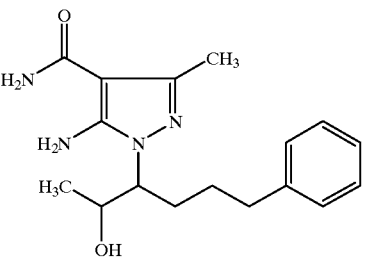

3.7 g (12.37 mmol) of 5-amino-1-[1-(1-hydroxy-ethyl)-4-phenyl-butyl]-3methyl-1H-pyrazole-4-carbonitrile and 950 mg of tetrabutylammonium hydrogen sulphate are dissolved in 25 ml of CH$_2$Cl$_2$, 5.5 ml of 5M NaOH and 7 ml of 30% strength H$_2$O$_2$ are added, and the mixture is stirred for 15 hours at room temperature. The phases are separated, the organic phase is extracted twice with water, the organic phase is dried over Na$_2$SO$_4$, and the solvent is removed in vacuo. Yield: 3.24 g (83%), $R_f$=0.11 (petroleum ether/ethyl acetate=1:1)

EXAMPLE XIV

5-Amino-4-cyano-3-methoxy-1-[(5-phenyl)-pent-2-yl]-pyrazole

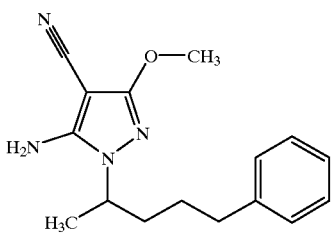

3.6 g of 2-hydrazino-5-phenylpentane are dissolved in 40 ml of methanol, and 2.8 ml of triethylamine are added. Then, 2.8 g of 1,1-dimethoxy-2,2-dicyanoethylene are added at approx. 0° C. The reaction solution is warmed to approx. 20° C. and stirred for 1.5 hours at approx. 20° C. For work-up, the mixture is diluted with water, acidified with citric acid and extracted twice with dichloromethane. The combined dichloromethane phases are dried with magnesium sulphate and evaporated in vacuo. This gives 5.1 g of a yellow oil, which crystallizes slowly. The oil is chromatographed on silica gel (Merck Si 60 0.04–0.063 mm) with a petroleum ether/ethyl acetate mixture in a ratio of 5:1 to 1:1. This gives a fraction which, after evaporation in vacuo, affords 4.6 g (=80.9% of theory) of 5-amino-4-cyano-3-methoxy-1-[(5-phenyl)-pent-2-yl]-pyrazole.

NMR(400 MHZ, CD30D): 1.3[3]d J=8 Hz; 1.4–1.65[3]m; 1.85–1.95[1]m; 2.5–2.65[2]m; 3.85[3]s; 4.1–4.2[1]m; 7.1–7.15[3]m; 7.2–7.25[2]m.

TLC RF value=0.6; eluent: petroleum ether/ethyl acetate 1:1; Merck Si60

EXAMPLE XV

5-Amino-4-cyano-3-methoxy-1-[2-hydroxy-6-phenyl-hex-3-yl]-pyrazole

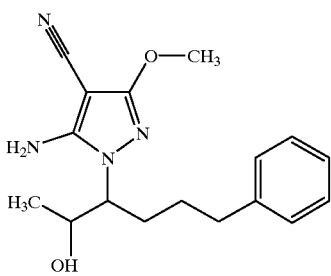

4.2 g of 3-hydrazino-2-hydroxy-6-phenylhexane are are dissolved in 20 ml of methanol, and 1.38 ml of triethylamine are added. Then, 1.38 g of 1,1-dimethoxy-2,2-dicyano-ethylene are added. The reaction solution is stirred for 2 hours at approx. 20° C. For work-up, the mixture is diluted with citric acid solution and ethyl acetate and extracted three times with ethyl acetate. The combined ethyl acetate phases are dried with magnesium sulphate and evaporated in vacuo. The evaporation residue is chromatographed on silica gel (Merck Si 60 0.04–0.063 mm) with a cyclohexane/ethyl acetate mixture in a ratio of 4:1 to 1:1. This gives a fraction which, after evaporation in vacuo, affords 0.959 g (=30.5% of theory) of 5-amino-4-cyano-3-methoxy-1-[2-hydroxy-6-phenyl-hex-3-yl]-pyrazole as diastereomer mixture.

TLC RF value=0.2; eluent: dichloromethane/methanol 10:1; Merck Si60 Art.No. 1.05719

EXAMPLE XVI tert-Butyl N'-(1-methyl-heptylidene)-hydrazinecarboxylate

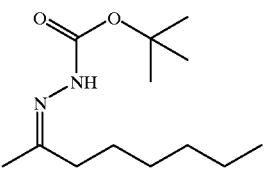

40 g (312 mmol) of 2-octanone and 41.23 g (312 mmol) of tert-butyl carbazate are refluxed for 2 hours in 350 ml of cyclohexane. The solvent and water are removed in vacuo. This gives 74.10 g (98%) of a waxy solid.

200 MHz $^1$H NMR (2 isomers) (ppm, CDCl$_3$):7.49, s, broad, 1H; 7.38, s, broad, 1H; 2.29, m, 2H; 2.12, m, 2H; 2.00, s, 3H; 1.79, s, 3H; 1.51, m, 11H; 1.29, m, 6H; 0.88, m, 3H.

EXAMPLE XVII tert-Butyl N'-(1-ethyl-heptylidene)-hydrazinecarboxylate

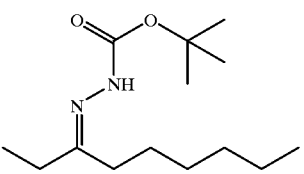

16.42 g (115 mmol) of 3-nonanone and 15.26 g (115.4 mmol) of tert-butyl carbazate are refluxed for 3 hours in 200 ml of cyclohexane. The solvent is removed in vacuo. This gives 30.54 g (product contains water) of a white solid, R$_f$=0.49 (cyclohexane/ethyl acetate=3:1).

EXAMPLE XVIII tert-Butyl N'-(1-propyl-heptylidene)-hydrazinecarboxylate

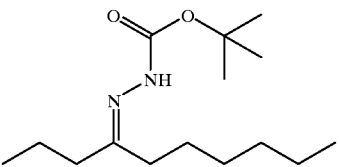

24.76 g (158 mmol) of 4-decanone and 20.94 g (158 mmol) of tert-butyl carbazate are heated for 90 minutes at 80° C. in 250 ml of cyclohexane/heptane mixture (1:1). After cooling, 39.71 g (93%) of a white solid are obtained by crystallization.

200 MHz $^1$H NMR (ppm, CDCl$_3$): 7.49, s, broad, 1H; 2.20, m, 4H 1.51, m, 13H; 1.30, m, 6H; 0.91, m, 6H.

EXAMPLE XIX (1-Methyl-heptyl)-hydrazine

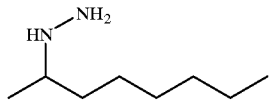

74.08 g (305.7 mmol) of tert-butyl N'-(1-methyl-heptylidene)-hydrazinecarboxylate are dissolved in a mixture of 235 ml of THF and 310 ml of methanol and, after 22.34 g (354.6 mmol) of sodium cyanoborohydride have been added, the mixture is stirred for 1 hour at room temperature. 213 ml of 6N HCl are added dropwise and, after the addition has ended, the mixture is refluxed for 1.5 hours. It is neutralized with 6N NaOH solution, then, after the non-aqueous solvents have been removed, extracted three times with dichloromethane, and, after the mixture has been dried over sodium sulphate, the solvent is removed in vacuo. This gives 37.5 g (85%) of a yellow oil.

400 MHz $^1$H NMR (ppm, CDCl$_3$): 3.18, s, broad, 3H; 2.52, m, 1H; 1.28, m, 9H; 1.07, d, 3H; 0.89, m, 4H.

EXAMPLE XX (1-Ethyl-heptyl)-hydrazine

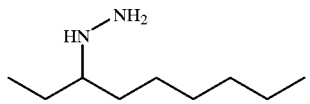

34.84 g (135.9 mmol) of tert-butyl N'-(1-ethyl-heptylidene)-hydrazinecarboxylate are dissolved in a mixture of 100 ml of THF and 150 ml of methanol and, after 9.93 g (157.6 mmol) of sodium cyanoborohydride have been added, the mixture is stirred for 2 hours at room temperature. 97 ml of 6N HCl are added dropwise and, after the addition has ended, the mixture is refluxed for 1.5 hours. It is neutralized with 6N NaOH solution, then, after the non-aqueous solvents have been removed, extracted three times with dichloromethane, and, after the mixture has been dried over sodium sulphate, the solvent is removed in vacuo. This gives 19.78 g (92%) of a yellow oil.

200 MHz $^1$H NMR (ppm, CDCl$_3$); 3.68, s, broad, 3H, 2.48, m, 1H; 1.32, m, 12H; 0.90, m, 6H.

EXAMPLE XXI (1-Propyl-heptyl)-hydrazine

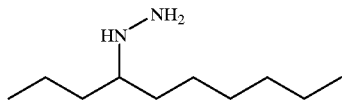

39.41 g (145.7 mmol) of tert-butyl N'-(1-propyl-heptylidene)-hydrazinecarboxylate are dissolved in a mixture of 100 ml of THF and 150 ml of methanol and, after 10.65 g (169 mmol) of sodium cyanoborohydride have been added, the mixture is stirred for 1 hour at room temperature. 100 ml of 6N HCl are added dropwise in the course of 30 minutes and, after the addition has ended, the mixture is refluxed for 1 hour. The mixture is neutralized with 6N NaOH solution, then, after the non-aqueous solvents have been removed, extracted three times with dichloromethane, and, after the mixture has been dried over sodium sulphate, the solvent is removed in vacuo. This gives 23.90 g (95%) of a yellow oil.

200 MHz $^1$H NMR (ppm, CDCl$_3$); 3.20, s, broad, 3H; 2.50, m, 1H; 1.20, m, 13H; 0.90, m, 6H.

EXAMPLE XXII

5-Amino-3-methyl-1-(2-octyl)-1-H-pyrazole-4-carboxamide

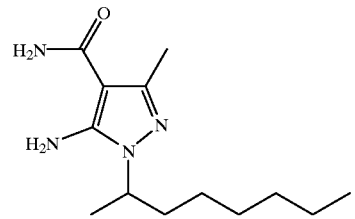

4.72 g (34.66 mmol) of 2-(1-ethoxy-ethylidene)-malononitrile and 5.00 g (34.66 mmol) of (1-methyl-heptyl)-hydrazine are refluxed for 4 hours in 40 ml of methanol. After the solvent has been removed in vacuo, 8.23 g of a red oil are obtained. This is dissolved in 250 ml of ethanol and, after 300 ml of concentrated NH$_3$ solution (25% strength) and 70 ml of hydrogen peroxide solution (30% strength) have been added, the solution is stirred for 65 hours at room temperature. After the non-aqueous solvents have been removed, the mixture is extracted three times with dichloromethane, and the organic phase is dried over sodium sulphate and evaporated on a rotary evaporator. This gives 7.75 g (87%) of a red oil.

EXAMPLE XXIII

5-Amino-3-ethyl-1-(2-octyl)-1-H-pyrazole-4-carboxamide

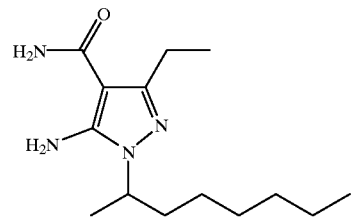

5.21 g (34.66 mmol) of 2-(1-ethoxy-propylidene)-malononitrile and 5.00 g (34.66 mmol) of (1-methyl-heptyl)-hydrazine are refluxed for 4 hours in 40 ml of methanol. After the solvent has been removed in vacuo, 8.60 g of a red oil are obtained. The latter is dissolved in 250 ml of ethanol and, after 300 ml of concentrated NH$_3$ solution (25% strength) and 70 ml of hydrogen peroxide solution (30%) have been added, the mixture is stirred for 48 hours at room temperature. After the non-aqueous solvents have been removed, the mixture is extracted three times with dichloromethane, and the organic phase is dried over sodium sulphate and evaporated on a rotary evaporator. This gives 7.45 g (71%) of a red solid.

EXAMPLE XXIV

5-Amino-3-methyl-1-(3-nonyl)-1-H-pyrazole-4-carboxamide

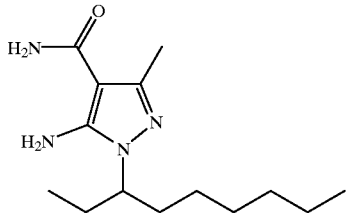

3.13 g (19.79 mmol) of (1-ethyl-heptyl)-hydrazine and 2.69 g (19.79 mmol) of 2-(1-ethoxy-ethylidene)-malononitrile are refluxed for 4 hours in 30 ml of methanol. After the solvent has been removed, 4.84 g of a red oil are obtained. The latter is dissolved in 150 ml of ethanol and, after 180 ml of concentrated $NH_3$ solution (35% strength) of 40 ml of hydrogen peroxide solution (30% strength) have been added, the mixture is stirred for 48 hours at room temperature. After the non-aqueous solvents have been removed, the mixture is extracted three times with dichloromethane, and the organic phase is dried over sodium sulphate and evaporated on a rotary evaporator. This gives 4.13 g (78%) of a red oil.

EXAMPLE XXV

5-Amino-3-ethyl-1-(3-nonyl)-1-H-pyrazole-4-carboxamide

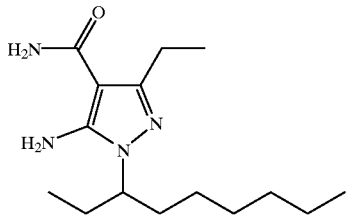

3.16 g (19.96 mmol) of (1-ethyl-heptyl)-hydrazine and 3.00 g (19.96 mmol) of 2-(1-ethoxy-propylidene)-malononitrile are refluxed for 4 hours in 30 ml of methanol. After the solvent has been removed, 5.102 g of a red oil are obtained. 4.70 g of this oil are dissolved in 150 ml of ethanol and, after 180 ml of concentrated $NH_3$ solution (25% strength) and 40 ml of hydrogen peroxide solution (30% strength) have been added, the solution is stirred for 65 hours at room temperature. After the non-aqueous solvents have been removed, the mixture is extracted three times with dichloromethane, and the organic phase is dried over sodium sulphate and evaporated on a rotary evaporator. This gives 4.83 g (96%) of a red oil.

EXAMPLE XXVI

5-Amino-3-methyl-1-(4-decyl)-1-H-pyrazole-4-carboxamide

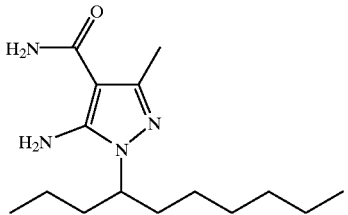

3.79 g (22 mmol) of (1-propyl-heptyl)-hydrazine and 2.99 g (22 mmol) of 2-(1-ethoxy-ethylidene)-malononitrile are refluxed for 4 hours in 30 ml of methanol. After the solvent has been removed, 5.86 g of a red oil are obtained. 5.19 g of this oil are dissolved in 150 ml of ethanol and, after 180 ml of concentrated $NH_3$ solution (25% strength) of 40 ml of hydrogen peroxide solution (30% strength) have been added, the mixture is stirred for 65 hours at room temperature. After the non-aqueous solvents have been removed, the mixture is extracted three times with dichloromethane, and the organic phase is dried over sodium sulphate and evaporated on a rotary evaporator. This gives 4.35 g (79%) of a yellow oil.

EXAMPLE XXVII

5-Amino-3-ethyl-1-(4-decyl)-1-H-pyrazole-4-carboxamide

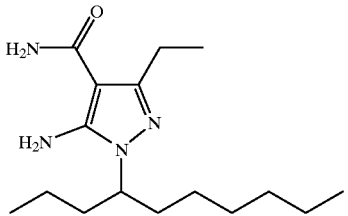

3.44 g (19.96 mmol) of (1-propyl-heptyl)-hydrazine and 3.0 g (19.96 mmol) of 2-(1-ethoxy-propylidene)-malononitrile are refluxed for 4 hours in 30 ml of methanol. After the solvent has been removed, 5.75 g of a red oil are obtained. 5.12 g of this oil are dissolved in 150 ml of ethanol and, after 180 ml of concentrated $NH_3$ solution (25% strength) and 40 ml of hydrogen peroxide solution (30% strength) have been added, the solution is stirred for 65 hours at room temperature. After the non-aqueous solvents have been removed, the mixture is extracted three times with dichloromethane, and the organic phase is dried over sodium sulphate and evaporated on a rotary evaporator. This gives 5.11 g (86%) of a yellow wax.

EXAMPLE XXVIII 2-(1-ethoxy-butylidene)-malononitrile

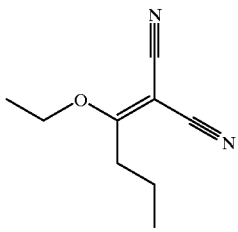

18.69 g (283 mmol) of malononitrile and 41.94 g (283 mmol) of triethylorthobutyrate are heated for 4 hours at 150° C. The reaction mixture is cooled to room temperature and, after the ethanol has been removed, distilled in vacuo. B.p.: 85° C. (3mbar).

Yield: 32.05 g (76%).

EXAMPLE XXIX

5-Amino-3-propyl-1-(4-decyl)-1-H-pyrazole-4-carboxamide

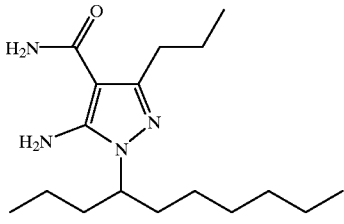

3.15 g (18.28 mmol) of (1-propyl-heptyl)-hydrazine and 3.0 g (18.28 mmol) of 2-(1-ethoxybutylidene)-malononitrile are refluxed for 4 hours in 30 ml of methanol. After the solvent has been removed, 5.57 g of a red oil are obtained. 4.99 g of this oil are dissolved in 150 ml of ethanol and, after 180 ml of concentrated $NH_3$ solution (25% strength) and 40 ml of hydrogen peroxide solution (30% strength) have been added, the solution is stirred for 65 hours at room temperature. After the non-aqueous solvents have been removed, the mixture is extracted three times with dichloromethane, and the organic phase is dried over sodium sulphate and evaporated on a rotary evaporator. The residue is dissolved in 150 ml of ethanol and, after 180 ml of concentrated $NH_3$ solution and 40 ml of hydrogen peroxide solution have been added, the solution is stirred for 65 hours at room temperature. After the non-aqueous solvents have been removed, the mixture is extracted three times with dichloromethane, and the organic phase is dried over sodium sulphate and evaporated on a rotary evaporator. This gives 4.89 g (92%) of a yellow oil.

EXAMPLE XXX

5-Amino-3-ethyl-1-(1-methyl-4-phenyl-butyl)-1-H-pyrazole-4-carboxamide

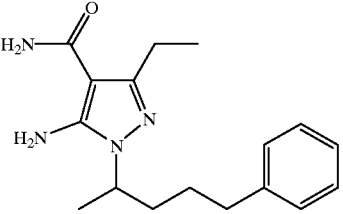

5.08 g (18 mmol) of 5-amino-3-ethyl-1-(1-methyl-4-phenyl-butyl)-1-H-pyrazole-4-carbonitrile are dissolved in 100 ml of ethanol and, after 100 ml of concentrated $NH_3$ solution (25% strength) and 50 ml of hydrogen peroxide solution (30% strength) have been added, the solution is stirred for 16 hours at room temperature. After the non-aqueous solvents have been removed, the pH is brought to 5 with 1N HCl. The aqueous phase is extracted three times with dichloromethane, and the organic phase is dried over sodium sulphate and evaporated on a rotary evaporator. This gives 3.58 g of a brown oil (66%).

EXAMPLE XXXI

5-Amino-1-[1-(1-hydroxy-ethyl)-4-phenyl-butyl]-3-ethyl-1H-pyrazole-4-carboxamide

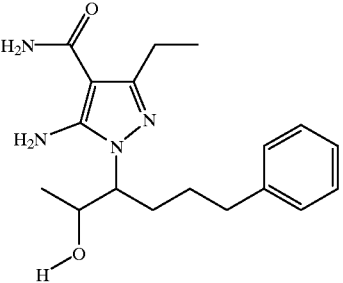

12.79 g (42 mmol) of tert-butyl N'-(1-methyl-4-phenyl-butylidene)-hydrazinecarboxylate are dissolved in 30 ml of THF and 40 ml of methanol, 6.08 g (97 mmol) of $NaBH_3CN$ are added, and the mixture is stirred for 60 minutes at room temperature. After 35 ml of 6N HCl have been added dropwise, the mixture is refluxed for 60 minutes. It is neutralized with 6N sodium hydroxide solution and extracted three times with $CH_2Cl_2$. The organic phase is dried over $Na_2SO_4$ and the solvent is removed in vacuo. This gives 7.38 g of a pale yellow oil. 3.00 g of this oil (14.4 mmol) and 2.50 g of 2-(1-ethoxy-propylidene)-malononitrile (16.6 mmol) are refluxed for 3 hours in 25 ml of methanol. The solvent is removed in vacuo. 4.238 g of a red oil. $R_f$=0.15. (PE/EA=2:1). This oil is dissolved in 136 ml of ethanol and, after 170 ml of concentrated $NH_3$ solution and 34 ml of 30% strength hydrogen peroxide solution have been added, the solution is stirred for 18 hours at room temperature. After the non-aqueous solvents have been removed in vacuo, the mixture is extracted three times with dichloromethane, the organic phase is dried over sodium sulphate, the solvent is removed in vacuo. This gives 2.55 g (53% strength) of a red oil. $R_f$=0.15 (PE/EA=1:1).

PREPARATION EXAMPLES

Example 1

6-Benzyl-1-(1-methyl-4-phenyl-butyl)-1,5-dihydro-pyrazolo[3,4-d]pyrimidin-4-ones

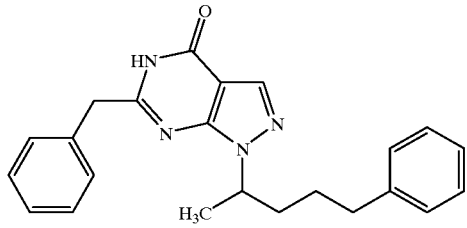

870 mg (3.42 mmol) of 5-amino-1-(1-methyl-4-phenyl-butyl)-1H-pyrazol-4-carbonitrile and 70 mg of DMAP are dissolved in 5 ml of pyridine, and a solution of 582 mg (3.78 mmol) of phenylacetyl chloride in 2 ml of toluene is added dropwise. The solution is stirred for 30 minutes at room temperature and for 2 hours at 60° C., the solvent is removed in vacuo, the residue is taken up in 50 ml of $CH_2Cl_2$, the organic phase is extracted with 1N HCl and saturated aqueous $NaHCO_3$ and dried over $Na_2SO_4$, and the solvent is removed in vacuo.

The residue is refluxed for 15 hours in 30 ml of water and 16 ml of ethanol together with 2 g of $K_2CO_3$ and 4 ml of 30% strength $H_2O_2$. After the reaction mixture has been acidified with 1N HCl, it is extracted with ethyl acetate, the organic phase is dried over $Na_2SO_4$ and the solvent is removed in vacuo. Purification by chromatography (petroleum ether/ethyl acetate) gives 450 mg (35%) of a solid. M.p.: 136° C.

The compounds listed in Table 1 are obtained analogously to the protocol of Example 1:

TABLE 1

| Ex. No. | Structure | F °C./$R_f$ | Yield (% of Theory) |
|---|---|---|---|
| 2 | 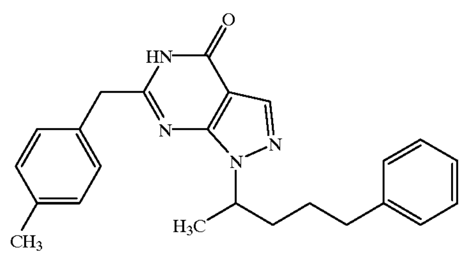 | 158 | 456 mg (42%) |
| 3 | 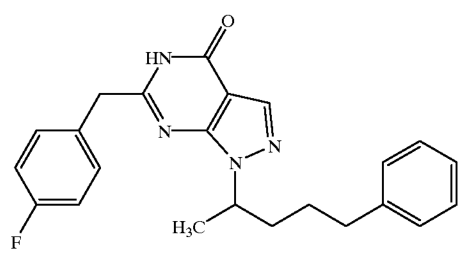 | 163 | 398 mg (36%) |
| 4 | 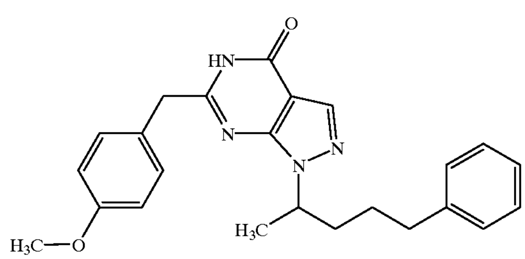 | 104 | 353 mg (32%) |

TABLE 1-continued

| Ex. No. | Structure | F °C./$R_f$ | Yield (% of Theory) |
|---|---|---|---|
| 5 | 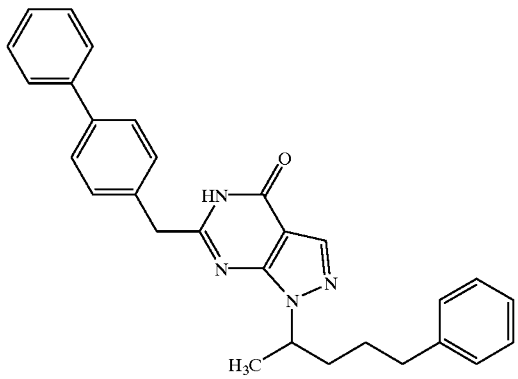 | 167 | 164 mg (14%) |
| 6 | 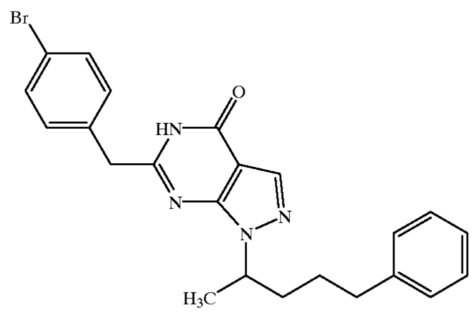 | 203 | 196 mg (2.5%) |

Example 7

6-(4-Chloro-benzyl)-1-(1-methyl-4-phenyl-butyl)-1,5-dihydro-pyrazolo[3,4-d]pyrimidin-4-ones

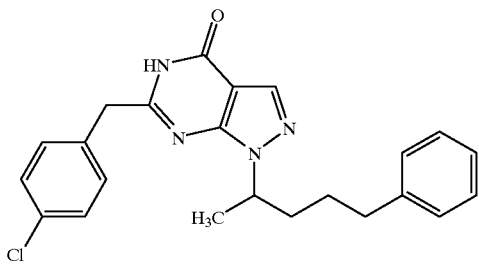

400 mg (1.47 mmol) of 5-amino-1-(1-methyl-4-phenyl-butyl)-1H-pyrazole-4-carboxamide and 80 mg of DMAP are dissolved in 12 ml of pyridine, and a solution of 457 mg (2.43 mmol) of p-chlorophenylacetyl chloride in 1 ml of toluene is added dropwise. The solution is stirred for 3.5 hours at 60° C., the solvent is removed in vacuo, the residue is taken up in 50 ml of $CH_2Cl_2$, the organic phase is extracted with 1N HCl and saturated aqueous $NaHCO_3$ and dried over $Na_2SO_4$, and the solvent is removed in vacuo.

The residue is refluxed for 3 hours in 4 ml of water, 15 ml of methanol and 7 ml of ethanol together with 700 mg of NaOH. The non-aqueous solvents are removed in vacuo, the residue is acidified with 1N HCl and then extracted with ethyl acetate, the organic phase is dried over $Na_2SO_4$, and the solvent is removed in vacuo. Purification by chromatography (petroleum ether/ethyl acetate) gives 380 mg (64%) M.p.: 168° C.

The compounds listed in Table 2 are obtained analogously to the protocol of Example 7:

TABLE 2

| Ex. No. | Structure | F °C./R$_f$ | Yield (% of Theory) |
|---|---|---|---|
| 8 | 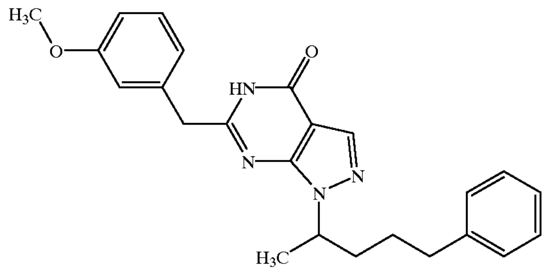 | 56 | 820 mg (85%) |
| 9 | 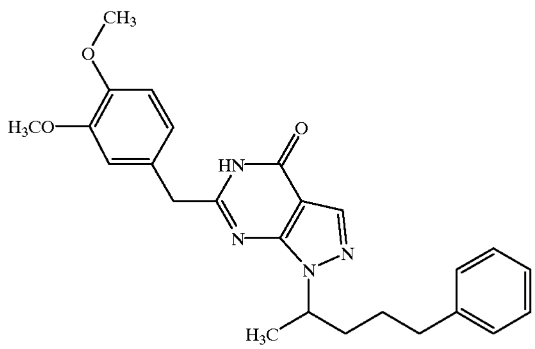 | 125 | 782 mg (79%) |
| 10 | 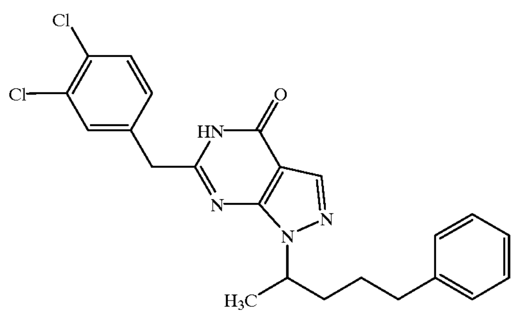 | 56 | 800 mg (76%) |

Example 11

6-(4-Bromo-benzyl)-1-(1-methyl-4-phenyl-butyl)-3-ethyl-1,5-dihydro-pyrazole[3,4-d]pyrimidin-4-one

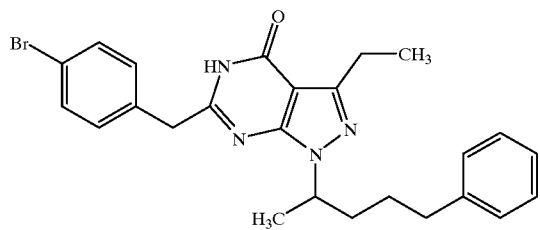

2.93 g (10.39 mmol) of 5-amino-3-ethyl-1-(1-methyl-4-phenyl-butyl)-1-H-pyrazole-4-carbonitrile and 250 mg of 4-dimethylaminopyridine are dissolved in 24 ml of pyridine, and a solution of 2.91 g (12.54 mmol) of 4-bromophenylacetyl chloride in 7 ml of toluene is added. The mixture is stirred for 2.5 hours at 60° C., the solvent is removed in vacuo, and the residue is taken up in 100 ml of CH$_2$Cl$_2$. The mixture is extracted with 1N HCl, saturated NaHCO$_3$ solution and water, the extract is dried over Na$_2$SO$_4$, and the solvent is removed in vacuo. The crude product is dissolved in 24 ml of pyridine, and a solution of 2 g (8.62 mmol) of 4-bromophenylacetyl chloride in 5 ml of toluene is added. The mixture is stirred for 2.5 hours at 60° C., the solvent is removed in vacuo, the residue is taken up in 100 ml of CH$_2$Cl$_2$. The mixture is extracted with 1N HCl, saturated NaHCO$_3$ solution and water, the extract is dried over Na$_2$SO$_4$, and the solvent is removed in vacuo.

The reaction product is dissolved in 370 ml of ethanol and, after 600 ml of 1N NaOH and 70 ml of H$_2$O$_2$ (30% strength) have been added, the solution is stirred for 5 hours at 90° C. The solvent is removed in vacuo, 1N HCl is added and the mixture then extracted three times with CH$_2$Cl$_2$, the extract is dried over Na$_2$SO$_4$ and the solvent is removed in vacuo. Purification by chromatography (CH$_2$Cl$_2$/methanol= 20:1) and crystallization from ether give 150 mg (3%) of a colourless solid.

M.p.: 112° C.

Example 12

6-(3'-Amino-biphenyl-4-yl-methyl)-3-ethyl-1-(1-methyl-4-phenyl-butyl)-1,5-dihydro-pyrazolo[3,4-d]pyrimidin-4-one

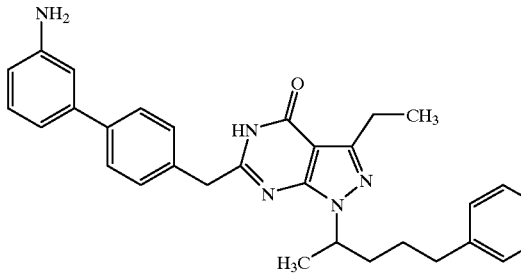

697 mg (4.5 mmol) of 3-aminophenylboronic acid monohydrate and 150 mg of tetrakistriphenylphosphine-palladium are added under argon to a solution of 1.66 g (3.47 mmol) of 6-(4-bromo-benzyl)-1-(1-methyl-4-phenyl-butyl)-3-ethyl-1,5-dihydro-pyrazolo[3,4-d]pyrimidin-4-one in 38 ml of THF, and the mixture is stirred for one hour at 70° C. After 4.9 ml of 1N $Na_2CO_3$ solution have been added, the mixture is stirred for a further 4 hours at 70° C., the solvent is removed in vacuo, and the residue is taken up in $CH_2Cl_2$. The mixture is extracted with 2N HCl, and the aqueous phase is rendered alkaline with 1N NaOH and extracted twice with $CH_2Cl_2$. After the extract has been dried over $Na_2SO_4$, the solvent is removed in vacuo. Purification by chromatography (toluene/ethyl acetate=4:1) gives 110 mg (6.4%) of a pale yellow solid.

M.p.: 108° C.

Example 13

6-Benzyl-1-[1-(1-hydroxy-ethyl)-4-phenyl-butyl]-1,5-dihydro-pyrazolo[3,4-d]pyrimidin-4-one

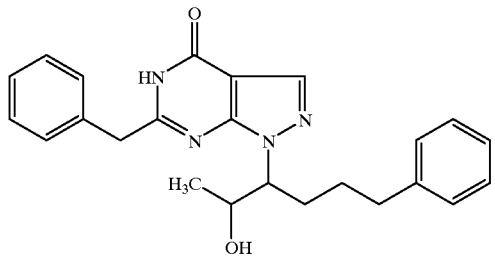

230 mg (0.76 mmol) of 5-amino-1-[1-(1-hydroxy-ethyl)-4-phenyl-butyl]-1H-pyrazole-4-carboxamide and 50 mg of 4-dimethylaminopyridine are dissolved in 5 ml of pyridine, and a solution of 293 mg (1.9 mmol) of phenylacetal chloride in 0.5 ml of toluene is added. The mixture is stirred for 3 hours at 50° C., the solvent is removed in vacuo, and the residue is taken up in 100 ml of $CH_2Cl_2$. The mixture is extracted with 1N HCl, saturated in $NaHCO_3$ solution and water, the extract is dried over $Na_2SO_4$, the solvent is removed in vacuo.

The reaction product is dissolved in 8 ml of methanol and 2 ml of ethanol, 2 ml of water and 350 mg of NaOH are added, and the mixture is refluxed for 3 hours. The solvents are removed in vacuo, 1 N HCl is added and the mixture is then extracted twice with EtOAc, the extract is dried over $Na_2SO_4$ and the solvent is removed in vacuo. Purification by chromatography (PE/EA=2:1) gives 101 mg (33%) of a diastereomer mixture, $R_f$=0.09 (PE/EA=1:1) and 10 mg (3.3%) of the pure diasteromer, which elutes later.

Example 14 and Example 15

6-(3,4-Dichloro-benzyl)-1-[1-(1-hydroxy-ethyl)-4-phenyl-butyl]-1,5-dihydro-pyrazolo-[3,4-d]pyrimidin-4-one

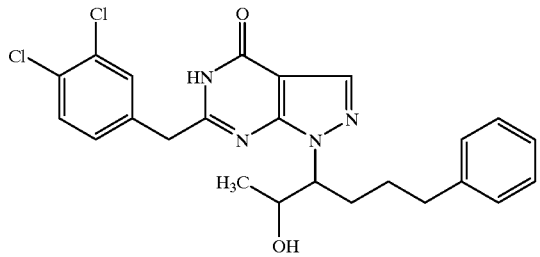

Starting from 400 g (1.32 mmol) of 5-amino-1-[1-(1-hydroxy-ethyl)-4-phenyl-butyl]-1H-pyrazole-4-carboxamide and 735 mg (3.31 mmol) of 3,4-dichlorophenylacetal chloride, the title compound is prepared analogously to the protocol of Example 13. This gives 65 mg (10.4%) of the diastereomer which elutes more rapidly, M.p.: 172° C., and 63 mg (10%) of the diastereomer which elutes more slowly, M.p.: 161° C.

Example 16 and Example 17

1-[1-(1-Hydroxy-ethyl)-4-phenyl-butyl]-6-(4-methyl-benzyl)-1,5-dihydro-pyrazolo[3,4-d]-pyrimidin-4-one

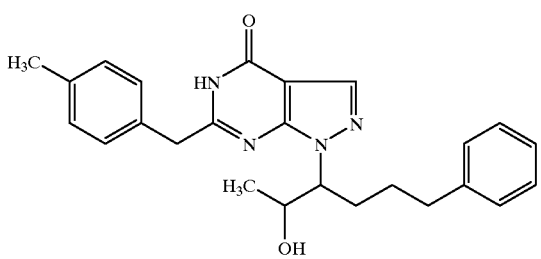

Starting from 400 g (1.32 mmol) of 5-amino-1-[1-(1-hydroxy-ethyl)-4-phenyl-butyl]-1H-pyrazole-4-carboxamide and 578 mg (3.44 mmol) of 4-methylphenylacetylchloride, the title compound is prepared analogously to the protocol of Example 13. This gives 117 mg (21%) of the diastereomer which elutes more rapidly, M.p.: 133° C., and 75 mg (13.6%) of the diastereomer which elutes more slowly, M.p.: 136° C.

Example 18

6-(3,4-Dimethoxy-benzyl)-1-[1-(1-hydroxy-ethyl)-4-phenyl-butyl]-1,5-dihydro-pyrazolo-[3,4-d]pyrimidin-4-one

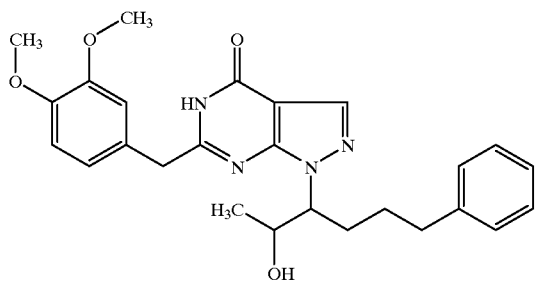

Starting from 400 mg (1.32 mmol) of 5-amino-1-[1-(1-hydroxy-ethyl)-4-phenyl-butyl]-1H-pyrazol-4-carboxamide and 711 mg (3.32 mmol) of 3,4-dimethoxyphenylacetylchloride, the title compound is obtained analogously to the protocol of Example 13.

Yield: 303 mg (50%).

M.p.: 85° C.

Example 19 and Example 20

6-(4-Fluoro-benzyl)-1-[1-(1-hydroxy-ethyl)-4-phenyl-butyl]-1,5-dihydro-pyrazolo-[3,4-d]pyrimidin-4-one

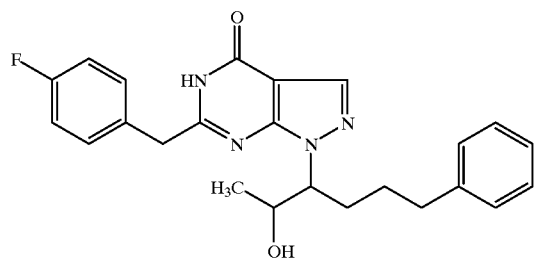

Starting from 400 mg (1.32 mmol) of 5-amino-1-[1-(1-hydroxy-ethyl)-4-phenyl-butyl]-1H-pyrazole-4-carboxamide and 570 mg (3.31 mmol) of 4-fluorophenylacetyl chloride, the title compounds are prepared analogously to the protocol of Example 13. This gives 143 mg (27%) of the diastereomer which elutes more rapidly, M.p. 103° C., and 111 mg (21%) of the diastereomer which elutes more slowly, M.p.: 107° C.

Example 21 and Example 22

6-(4-chloro-benzyl)-1-[1-(1-hydroxy-ethyl)-4-phenyl-butyl]-1,5-dihydro-pyrazolo-[3,4-d]pyrimidin-4-one

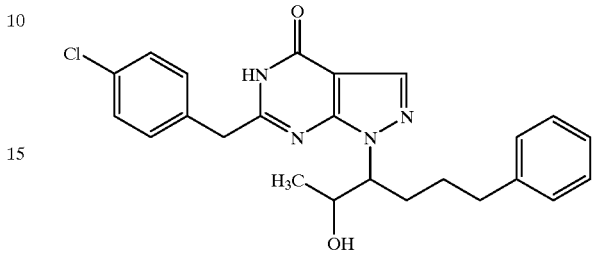

Starting from 400 mg (1.32 mmol) of 5-amino-1-[1-(1-hydroxy-ethyl)-4-phenyl-butyl]-1H-pyrazole-4-carboxamide and 626 mg (3.77 mmol) of 4-chlorophenylacetyl chloride, the title compounds are prepared analogously to the protocol of Example 13. This gives 150 mg (26%) of the diastereomer which elutes more rapidly, M.p.: 125° C., and 90 mg (16%) of the diastereomer which elutes more slowly, M.p.: 101° C.

Example 23 and Example 24

1-[1-(1-hydroxy-ethyl)-4-phenyl-butyl]-6-(3-methoxy-benzyl)-1,5-dihydro-pyrazolo-[3,4-d]pyrimidin-4-one

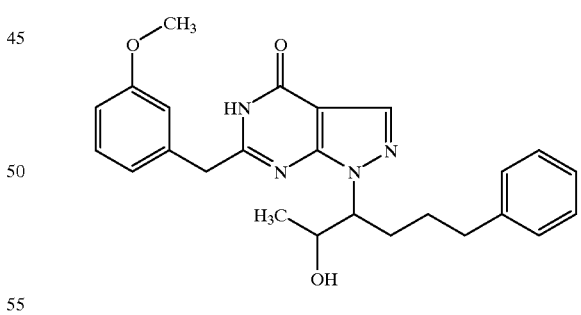

Starting from 400 mg (1.32 mmol) of 5-amino-1-[1-(1-hydroxy-ethyl)-4-phenyl-butyl]-1H-pyrazole-4-carboxamide and 610 mg (3.81 mmol) of 3-methoxyphenylacetyl chloride, the title compounds are prepared analogously to the protocol of Example 13. This gives 160 mg (28%) of the diastereomer which elutes more rapidly, M.p.: 92° C., and 145 mg (25%) of the diastereomer which elutes more slowly, M.p.: 54° C.

Example 25 and Example 26

6-biphenyl-4-yl-methyl-1-[1-(1-hydroxy-ethyl)-4-phenyl-butyl]-1,5-dihydro-pyrazolo-[3,4-d]pyrimidin-4-one

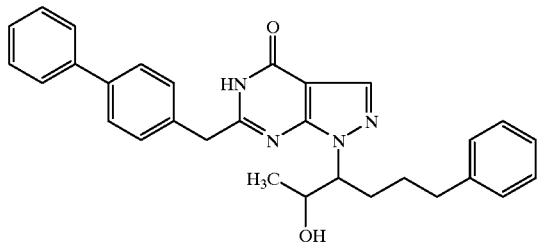

Starting from 954 mg (3.16 mmol) of 5-amino-1-[1-(1-hydroxy-ethyl)-4-phenyl-butyl]-1H-pyrazole-4-carboxamide and 1.82 g (7.91 mmol) of 4-phenylphenylacetyl chloride, the title compounds are prepared analogously to the protocol of Example 13. This gives 410 mg (27%) of the diastereomer which elutes more rapidly, M.p.: 90° C., and 160 mg (11%) of the diastereomer which elutes more slowly, M.p.: 142° C.

Example 27 and Example 28

1-[1-(1-Hydroxy-ethyl)-4-phenyl-butyl]-6-(4-methoxy-benzyl)-1,5-dihydro-pyrazolo-[3,4-d]pyrimidin-4-one

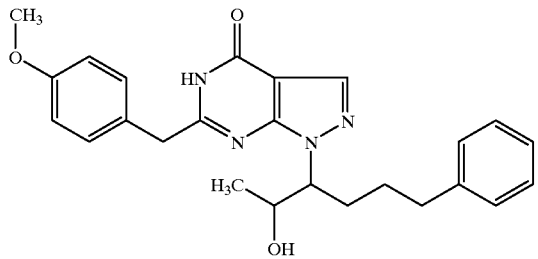

Starting from 1 g (3.31 mmol) of 5-amino-1-[1-(1-hydroxy-ethyl)-4-phenyl-butyl]-1H-pyrazole-4-carboxamide and 1.52 g (8.26 mmol) of 4-methoxyphenylacetyl chloride, the title compounds are prepared analogously to the protocol of Example 13. This gives 240 mg (17%) of the diastereomer which elutes more rapidly, M.p.: 41° C., and 134 mg (9%) of the diastereomer which elutes more slowly, M.p.: 48° C.

Example 29 and Example 30

6-(4-bromo-benzyl)-1-[1-(1-hydroxy-ethyl)-4-phenyl-butyl]-1,5-dihydro-pyrazolo-[3,4-d]pyrimidin-4-one

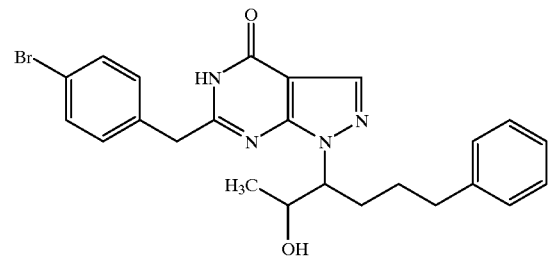

Starting from 2.1 g (6.95 mmol) of 5-amino-1-[1-(1-hydroxy-ethyl)-4-phenyl-butyl]-1H-pyrazole-4-carboxamide and 4.05 mg (17.38 mmol) of 4-bromophenylacetyl chloride, the title compounds are prepared analogously to the protocol of Example 13. This gives 594 mg (18%) of the diastereomer which elutes more rapidly, M.p.: 117° C., and 372 mg (11%) of the diastereomer which elutes more slowly, M.p.: 116° C.

Example 31

1-[1-(1-Hydroxy-ethyl)-4-phenyl-butyl]-6-(hydroxy-phenyl-methyl)-1,5-dihydro-pyrazolo-[3,4-d]pyrimidin-4-one

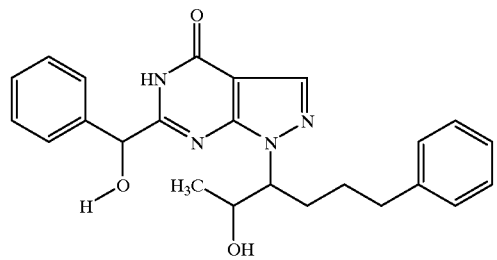

Starting from 1.25 g (4.14 mmol) of 5-amino-1-[1-(1-hydroxy-ethyl)-4-phenyl-butyl]-1H-pyrazole-4-carboxamide and 2.20 mg (10.38 mmol) of D,L-acetylmandelyl-chloride gives the title compound in a yield of 72 mg (4.2%).

$R_f$=0.10 (cyclohexane/ethyl acetate=2:1).

Example 32 and Example 33

6-Benzyl-1-[1-(1-hydroxy-ethyl)-4-phenyl-butyl]-3-methyl-1,5-dihydro-pyrazolo[3,4-d]pyrimidin-4-one

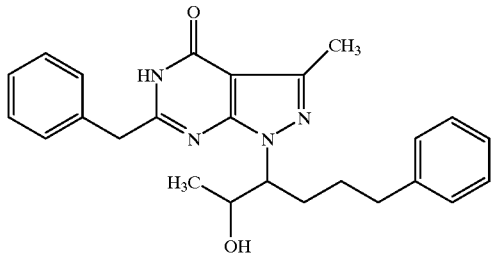

805 mg (2.55 mmol) of 5-amino-1-[1-(1-hydroxy-ethyl)-4-phenyl-butyl]-3-methyl-1H-pyrazole-4-carboxamide and 140 mg of 4-dimethylaminopyridine are dissolved in 20 ml of pyridine, and a solution of 991 mg (6.48 mmol) of phenylacetal chloride in 1 ml of toluene is added. The mixture is stirred for 3 hours at 50° C., the solvent is removed in vacuo, and the residue is taken up in 100 ml of $CH_2Cl_2$. The mixture is extracted with 1N HCl, saturated in $NaHCO_3$ solution and water, the extract is dried over $Na_2SO_4$, and the solvent is removed in vacuo.

The reaction product is dissolved in 45 ml of ethanol, 8 ml of water and 2.0 g of NaOH are added, and the mixture is refluxed for 3 hours. The solvents are removed in vacuo, 1N HCl is added and the mixture is then extracted twice with EtOAc, the extract is dried over $Na_2SO_4$ and the solvent is removed in vacuo. Purification by chromatography (PE/EA= 2:1) gives 216 mg (20%) of a diastereomer with elutes more rapidly, $R_f$=0.2 (cyclohexane/ethyl acetate=2:1) and 156 mg (15%) of the diasteromer which elutes more slowly, $R_f$=0.1 (cyclohexane/ethyl acetate=2:1).

Example 34 and Example 35

6-(3,4-Dichloro-benzyl-1-[1-(1-hydroxy-ethyl)-4-phenyl-butyl]-3-methyl-1,5-dihydro-pyrazolo[3,4-d]pyrimidin-4-one

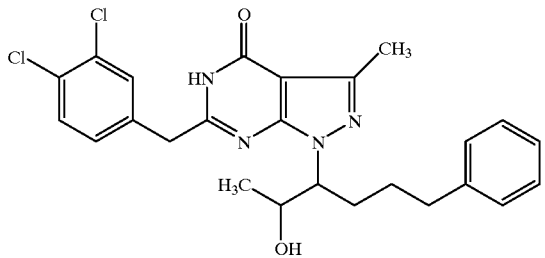

Starting from 805 mg (2.55 mmol) of 5-amino-1-[1-(1-hydroxy-ethyl)-4-phenyl-butyl]-3-methyl-1H-pyrazole-4-carboxamide and 1.41 g (6.59 mmol) of 3,4-dichlorophenylacetyl chloride, are employed analogously to the protocol of Example 32 and 33. This gives 217 mg (18%) of the diastereomer which elutes more rapidly, $R_f$=0.2 (cyclohexane/ethyl acetate=2:1) and 186 mg (15%) of the diastereomer which elutes more slowly, M.p.: 160° C.

Example 36

6-(3,4-Dimethoxy-benzyl-1-[1-(1-hydroxy-ethyl)-4-phenyl-butyl]-3-methyl-1,5-dihydro-pyrazolo[3,4-d]pyrimidin-4-one

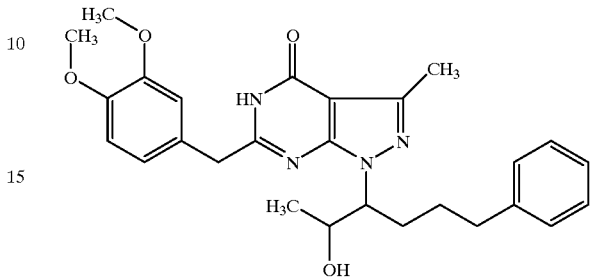

The title compound is obtained starting from 805 mg (2.55 mmol) of 5-amino-1-[1-(1-hydroxy-ethyl)-4-phenyl-butyl]-3-methyl-1H-pyrazole-4-carboxamide and 1.37 g (6.40 mmol) of 3,4-dimethoxyphenyl acetyl chloride.

Yield: 139 mg (9%)

$R_f$=0.1 (cyclohexane/ethyl acetate=2:1).

Example 37

1-(1-Acetyl-4-phenyl-butyl)-6-(4-methoxy-benzyl)-1,5-dihydro-pyrazolo[3,4-d]pyrimidin-4-one

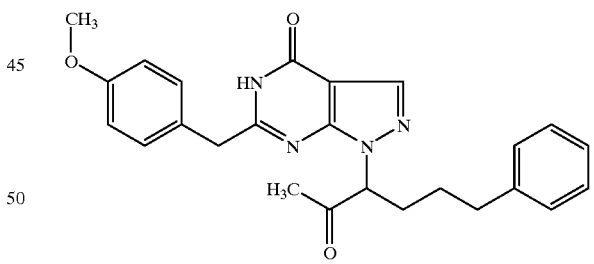

151 mg (0.35 mmol) of 1-[1-(-hydroxy-ethyl)-4-phenyl-butyl]-6-(4-methoxy-benzyl)-1,5-dihydro-pyrazolo[3,4-d]pyrimidin-4-one are dissolved in 1 ml of DMSO and 3.5 ml of dichloromethane, and the solution is cooled to 0° C. 0.485 ml of triethylamine and 245 mg of $SO_3$/pyridine complex are added, and the mixture is stirred for 15 hours at room temperature. The mixture is diluted with 20 ml of dichloromethane, extracted with 1N HCl and saturated $NaHCO_3$ solution, the extract is dried over $Na_2SO_4$, and the solvent is removed in vacuo. Purification by chromatography (PE-EA=2:1) gives 115 mg (76%), M.p.: 129° C.

Example 38

1-(1-Acetyl-4-phenyl-butyl)-6-biphenyl-4-ylmethyl-1,5-dihydro-pyrazolo[3,4-d]pyrimidin-4-one

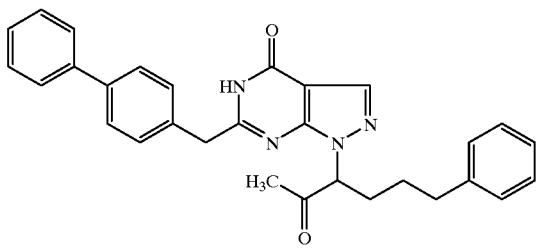

The title compound is obtained starting from 299 mg (0.62 mmol) of 6-biphenyl-4-yl-methyl-1-[1-(1-hydroxy-ethyl)-4-phenyl-butyl]-1,5-dihydro-pyrazolo[3,4-d]-pyrimidin-4-one in a yield of 268 mg (91%).

M.p.: 107° C.

Example 39

1-(1-Acetyl-4-phenyl-butyl)-6-(3,4-dimethoxy-benzyl)-3-methyl-1,5-dihydro-pyrazolo[3,4-d]pyrimidin-4-one

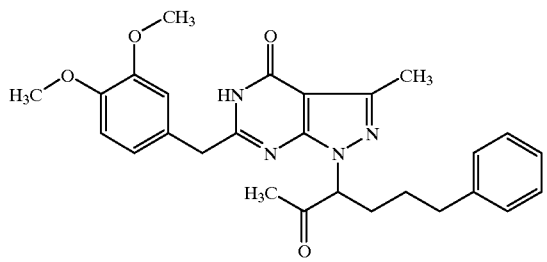

The title compound is obtained starting from 237 mg (0.51 mmol) of 6-(3,4-dimethoxy-benzyl-1-[1-(1-hydroxy-ethyl)-4-phenyl-butyl]-3-methyl-1,5-dihydro-pyrazolo[3,4-d]-pyrimidin-4-one in a yield of 165 mg (70%).

M.p.: 120° C.

Example 40

6-[4-Morpholine-4-sulphonyl)-benzyl][1-(1-hydroxy-ethyl)-4-phenyl-butyl]-3-methyl-1,5-dihydro-pyrazolo[3,4-d]pyrimidin-4-one

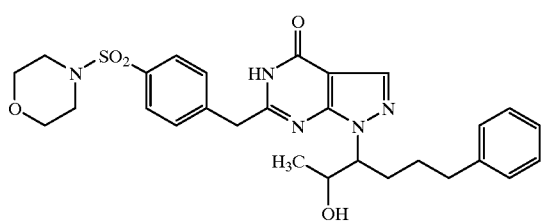

785 mg (2.48 mmol) of 5-amino-1-[1-(1-hydroxy-ethyl)-4-phenyl-butyl]-3-methyl-1H-pyrazole-4-carboxamide, 1.40 g of potassium tert-butoxide and 1.67 g (5.58 mmol) of methyl 4-(morpholinosulphonyl)-phenylacetate are refluxed overnight in 18 ml of ethanol. The solvent is removed in vacuo, taken up in dichloromethane, extracted with 1N HCl, and the organic phase is dried over $Na_2SO_4$ and evaporated on a rotary evaporator. Purification by chromatography (twice; dichloromethane/methanol=30/1), gives 375 mg (28%). $R_f$=0.33 (dichloromethane/methanol=30/1).

Example 41

1-(1-Acetyl-4-phenyl-butyl)-6-(4-(3-pyridyl)-benzyl)-1,5-dihydro-pyrazolo[3,4-d]pyrimidin-4-one

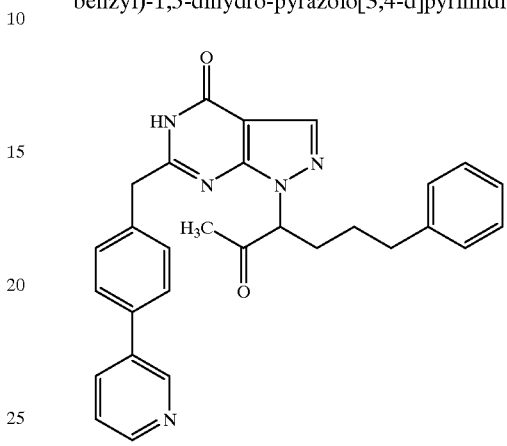

71 mg (0.48 mmol) of diethyl-(3-pyridyl)-borane and 16 mg of tetrakistriphenylphosphine-palladium are added under argon to a solution of 177 mg (0.37 mmol) of 1-(1-acetyl-4-phenyl-butyl)-6-(4-bromo-benzyl)-1,5-dihydro-pyrazolo[3,4-d]pyrimidin-4-one in 4 ml of THF, and the mixture is stirred for one hour at 70° C. After 0.522 ml of 2 N $Na_2CO_3$ solution have been added, the mixture is stirred for a further 4 hours at 70° C., a further 27 mg (0.185 mmol) of diethyl-(3-pyridyl)-borane and 16 mg of tetrakistriphenylphosphine-palladium are added, and the mixture is stirred for 14 hours under reflux. The solvent is removed in vacuo and the residue taken up in $CH_2Cl_2$. The mixture is extracted with 2N HCl, and the aqueous phase is rendered alkaline with 1N NaOH and extracted twice with $CH_2Cl_2$. After the mixture has been dried over $Na_2SO_4$, the solvent is removed in vacuo. Purification by chromatography (toluene/ethyl/acetate=4:1) gives 110 mg (6.4%) of a pale yellow solid.

M.p.: 108° C.

Example 42

6-Benzyl-3-methoxypyrazolo[3,4-d]pyrimidin-4(5H)-one

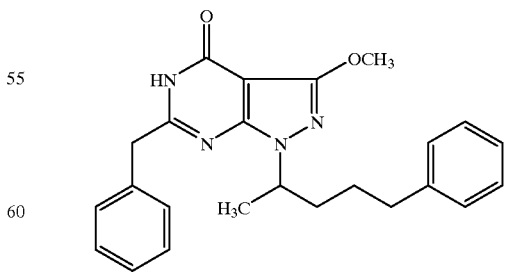

4.6 g of 5-Amino-4-cyano-3-methoxy-1-[(5-phenyl)-pent-2-yl]-pyrazole are dissolved in 25 ml of pyridine. 2.2 ml of phenylacetyl chloride are slowly added dropwise at approx. 0° C. The reaction mixture is stirred overnight at approx. 20° C. Then, a further 0.7 ml of phenylacetyl chloride are added, and stirring is continued for 2 hours. For work-up, the mixture is diluted with ethyl acetate and extracted twice with dilute citric acid solution. The ethyl acetate phase is dried with magnesium sulphate and evaporated in vacuo. This gives 7.5 g of a brown oil which is then heated at 100° C. in a mixture of 75 ml of 1N sodium hydroxide solution and 4.5 ml 35% strength hydrogen peroxide. For work-up, ice is added and the mixture is extracted twice with ethyl acetate. The combined ethyl acetate phases are washed with dilute thiosulphate solution and with dilute citric acid solution, dried with magnesium sulphate and evaporated in vacuo. This gives 5.1 g of a yellow oil which is chromatographed on silica gel (Merck Si 60 0.04–0.063 mm) with a cyclohexane/ethyl acetate mixture in a ratio of 100:0 to 1:1.5 fractions are obtained:

Fraction 1: 0.46 g of 4-cyano-3-methoxy-5-(phenylacetyl)amino-1-[5-phenyl-pent-2-yl]-pyrazole Fraction 2: 0.08 g of 5-amino-4-cyano-3-methoxy-1-[(5-phenyl)-pent-2-yl]-pyrazole Fraction 3: 2.0 g of 6-benzyl-3-methoxy-1-[5-phenyl-pent-2-yl]pyrazolo[3,4-d]-pyrimidin-4(5H)-one, contaminated with 5-amino-4-cyano-3-methoxy-1-[5-phenyl-pent-2-yl]pyrazole Fraction 4: 0.9 g of 6-benzyl-3-methoxy-1-[5-phenyl-pent-2-yl]pyrazolo[3,4-d]-pyrimidin-4(5H)-one Fraction 5: 0.5 g of 5-amino-4-carboxamido-3-methoxy-1-[5-phenyl-pent-2-yl]-pyrazole NMR of 6-benzyl-3-methoxy-1-[5-phenyl-pent-2yl]-pyrazolo[3,4-d]pyrimidin-4(5H)-one (fraction 4)
(300 MHZ, CD$_3$OD) 1.2–1.5[2]m; 1.4[3]d J=8 Hz; 1.6–1.75[1]m; 1.9–2.05[1]m;2–2.6[2]m; 3.9[2]s; 3.95[3]s; 4.75–4.85[1]m; 7.0[2]d; 7.05–7.35[8]m TLC of 6-benzyl-3-methoxy-1-[5-phenyl-pent-2yl]-pyrazolo[3,4-d]pyrimidin-4(5H)-one (fraction 4)
R$_f$ value=0.4; mobile phase: petroleum ether/ethyl acetate 1:1; Merck Si60 Art. No. 1.05719

NMR of 5-amino-4-carboxamido-3-methoxy-1-[5-phenyl-pent-2-yl]-pyrazole (fraction 5)
(300 MHZ, CD$_3$OD) 1.3[3]d J=8 Hz; 1.35–1.65[3]m 1.85–2.0[1]m; 2.5–2.65[2]m; 3.9[3]s; 4.1–4.2[1]m; 7.1–7.15[3]m; 7.2–7.25[2]m TLC of 5-amino-4-carboxamido-3-methoxy-1-[5-phenyl-pent-2-yl]-pyrazole (fraction 5)
R$_f$ value=0.16; mobile phase: petroleum ether/ethyl acetate 1:1; Merck Si60 Art. No. 1.05719

Example 43

6-Benzyl-1-[5-phenyl-pent-2yl]-pyrazolo[3,4-d]pyrimidin-3,4(2H,5H)-one

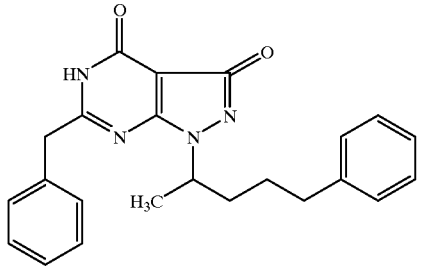

1.6 g of 6-Benzyl-3-methoxy-1-[5-phenyl-pent-2-yl]-pyrazolo[3,4-d]pyrimidin-4(5H)-one (fraction 3 in the abovementioned example), together with 0.75 g of sodium iodide are dissolved in 25 ml of absolute acetonitrile. After 0.63 ml of trimethylchlorosilane have been added, the mixture is refluxed for 2 hours. For work-up, the reaction mixture is poured into dilute sodium thiosulphate solution and extracted with ethyl acetate. The two-phase mixture contains the product as a white crystalline precipitate. The precipitate is filtered off with suction, washed with ethyl acetate and water and dried in vacuo. This gives 0.636 g (=61% of theory) of 6-benzyl-1-[5-phenyl-pent-2-yl]-pyrazolo[3,4-d]pyrimidin-3,4(2H,5H)-one, M.p.=275° C.

NMR of 6-benzyl-1-[5-phenyl-pent-2yl]-pyrazolo[3,4-d]pyrimidin-3,4(2H,5H)-one (200 MHZ, DMSO-d6) 1.1–1.4 [2]m; 1.3[3]d J=8 Hz; 1.55–1.9[2]m; 2.35–2.6[2]m; 3.85[2] s; 4.6–4.8[1]m; 7.0–7.4[10]m; 10.9[1]s broad; 11.9[1]s broad.

Example 44

6-(3,4-Dimethoxybenzyl)-3-methoxy-1-[5-phenyl-pent-2-yl]-pyrazolo[3,4-d]pyrimidin-4(5H)-one

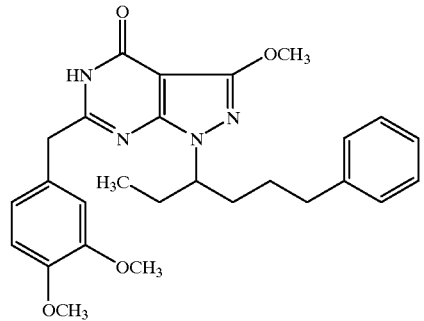

0.416 g of 5-amino-4-carboxamido-3-methoxy-1-[5-phenyl-pent-2-yl]-pyrazole together with 1.34 g of ethyl 3,4-dimethoxyphenylacetate and 1.18 g of potassium tert-butoxide is refluxed for 2 hours in 6 ml of absolute ethanol. For work-up, the mixture is diluted with ethyl acetate and washed twice with saturated sodium hydrogen carbonate solution. The ethyl acetate phase is dried with magnesium sulphate and evapoarated in vacuo. The evaporation residue crystallizes from diethyl ether. After filtration with suction and drying in vacuo, 0.528 g (=82.7% of theory) of 6-(3,4-dimethoxybenzyl)-3-methoxy-1-[5-phenyl-pent-2-yl]-pyrazolo[3,4-d]pyrimidin-4(5H)-one is obtained as white crystals, M.p.=148° C.

NMR (200 MHZ, CDCl$_3$) 1.45[3]d J=8 Hz; 1.35–1.55[2] m; 1.65–1.85[1]m; 1.95–2.15[1]m; 2.5–2.7[2]m; 3.8[3]s; 3.85[3]s; 3.95[2]s; 4.0[3]s; 4.75–4.90[1]m; 6.75[1]d J=8 Hz; 6.85–7.0[2]m; 7.1–7.3[5]m.

TLC R$_f$ value=0.5; mobile phase: dichloromethane/methanol 10:1, Merck Si60 Art. No. 1.05719

Example 45

6-Benzyl-3-methoxy-1-[2-hydroxy-(6-phenyl)-hex-3-yl]-pyrazolo[3,4-d]pyrimidin-4(5H)-one

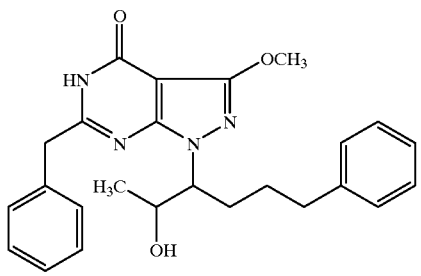

0.94 g of 5-amino-4-cyano-3-methoxy-1-[2-hydroxy-6-phenyl-hex-3-yl]-pyrazole is dissolved in 5 ml of pyridine. 0.98 ml of phenylacetal chloride is slowly added dropwise at approx. 0° C. The reaction mixture is stirred overnight at approx. 20° C. Then, a further 0.25 ml of phenyl acetal chloride are added and stirring is continued for 1 hour. For work-up, the mixture is diluted with ethyl acetate and extracted twice with dilute citric acid solution. The ethyl acetate phase is dried with magnesium sulphate and evaporated in vacuo. This gives 2.16 g of a brown oil which is then heated for 6 hours at 100° C. in a mixture of 15 ml of 1N sodium hydroxide solution and 0.78 ml of 35% strength hydrogen peroxide. For work-up, ice is added and the mixture is extracted twice with ethyl acetate. The combined ethyl acetate phases are washed with dilute thiosulphate solution and with dilute citric acid solution, dried with magnesium sulphate and evaporated in vacuo. This gives 2 g of an oil which is chromatographed on silica gel (Merck Si60 0.04–0.063 mm) with a cyclohexane/ethyl acetate mixture in a ratio of 50:0 to 2:1. This gives several fractions, of which one affords 0.185 g (=15% of theory) of 6-benzyl-3-methoxy-1-[2-hydroxy-(6-phenyl)-hex-3-yl]-pyrazolo[3,4-d]pyrimidin-4(5H)-one as diastereomer mixture after evaporation.

NMR (300 MHZ, CD$_3$OD) 0.9 and 1.1[3]d J=8 Hz; 1.2–1.4[2]m; 1.65–1.8 and 1.95–2.1[2]m; 2.4–2.7[2]m; 3.9 [3]s; 3.95[2]s; 4.0–4.1[1]m; 4.4–4.55[1]m; 6.95–7.35[10]m.

Example 46

6-(3,4-Methylenedioxy-benzyl)-1-(1-methyl-4-phenyl-butyl)-1,5-dihydro-pyrazolo[3,4-d]pyrimidin-4-one

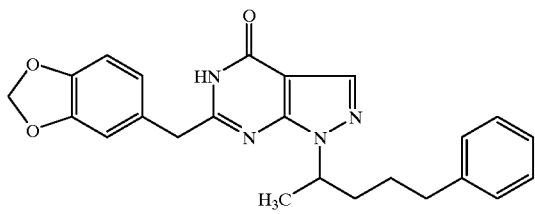

18 mg (0.066 mmol) of 5-amino-1-(1-methyl-4-phenyl-butyl)-1H-pyrazole-4-carboxamide and 41 mg (0.21 mmol) of methyl 3,4-methylenedioxyphenylacetate are refluxed for 6 hours in 1 ml of a 0.5M ethanolic potassium tert-butoxide solution. After dichloromethane and saturated aqueous sodium hydrogen carbonate solution have been added, the phases are separated. Purification by chromatography gives 18 mg (64%) of a solid, R$_f$=0.34 (dichloromethane/methanol=15:1).

Example 47

6-(3,4,5-Trimethoxy-benzyl)-1(1-methyl-4-phenyl-butyl)-3-ethyl-1,5-dihydro-pyrazolo[3,4-d]pyrimidin-4-one

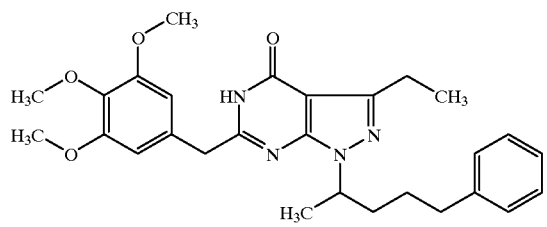

400 mg (1.4mmol) of 5-amino-3-ethyl-1-(1-methyl-4-phenyl-butyl)-1H-pyrazole-4-carboxamide, 750 mg (6.7 mmol) of potassium tert-butoxide and 720 mg (3.0 mmol) of methyl 3,4,5-trimethoxy-phenylacetate are refluxed for 16 hours in 10 ml of ethanol. After the solvent has been removed, the mixture is acidified with 1N HCl, extracted 3 times with dichloromethane, the organic phase is dried over sodium sulphate and the solvent is removed in vacuo. Purification by chromatography gives 286 mg (40%) of a solid, R$_f$=0.62 (ethyl acetate/cyclohexane=2:1).

Example 48

6-(3,4-Methylenedioxy-benzyl)-1-(1-methyl-4-phenyl-butyl)-3-ethyl-1,5-dihydro-pyrazolo[3,4-d]pyrimidin-4-one

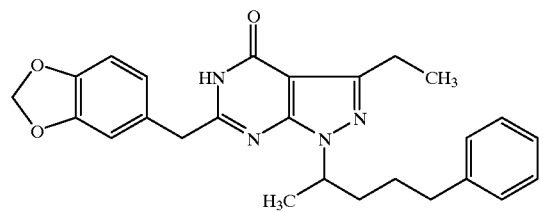

19 mg (0.063 mmol) of 5-amino-1-(1-methyl-4-phenyl-butyl)-3-ethyl-1H-pyrazole-4-carboxamide and 35 mg (0.180 mmol) of methyl 3,4-methylenedioxyphenylacetate are refluxed for 6 hours in 0.9 ml of 0.5M ethanolic potassium tert-butoxide solution. After dichloromethane and saturated aqueous sodium hydrogen carbonate solution have been added, the phases are separated. Purification by chromatography gives 14 mg (48%) of a solid, R$_f$=0.64 (dichloromethane/methanol=15:1).

Examples 49 and 50

6-(3,4-Dimethoxy-benzyl)-1-[1-(1-hydroxy-ethyl)-4-phenyl-butyl]-3-ethyl-1,5-dihydro-pyrazolo[3,4-d]pyrimidin-4-one

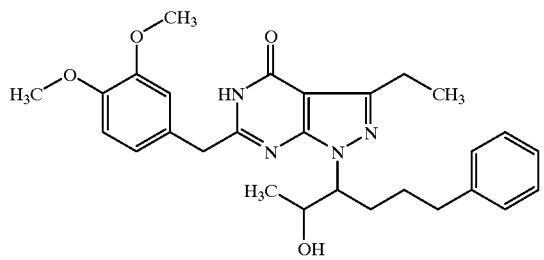

1.0 g (3.03 mmol) of 5-amino-1-[1-(1-hydroxy-ethyl)-4-phenyl-butyl]-3-ethyl-1H-pyrazole-4-carboxamide, 1.60 g of potassium tert-butoxide and 1.40 g (19 mmol) of methyl 3,4-dimethoxyphenylacetate are refluxed overnight in 20 ml of ethanol. The solvent is removed in vacuo, the residue is taken up in dichloromethane, the mixture is extracted with 1N HCl, the organic phase is dried over $Na_2SO_4$ and evaporated on a rotary evaporator. Purification by chromatography (cyclohexane/EA=2:1, 1% formic acid) and separation of the diastereomers by chromatography gives 232 mg (16%) of the diastereomer which elutes more rapidly, $R_f$=0.2 (cyclohexane/ethyl acetate=2:1) and 150 mg (10%) of the diastereomer which elutes more slowly, $R_f$=0.15 (cyclohexane/ethyl acetate=2:1).

Example 51

6-(3,4-methylenedioxy-benzyl)-1-[1-(1-hydroxy-ethyl)-4-phenyl-butyl]-3-ethyl-1,5-dihydro-pyrazolo[3,4-d]pyrimidin-4-one

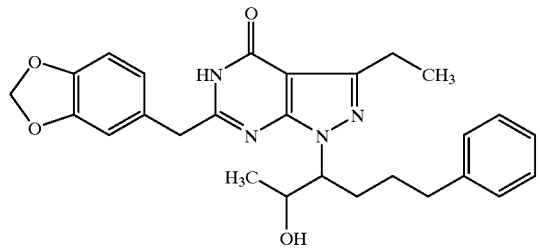

10 mg (0.037 mmol) of 5-amino-1-[1-(1-hydroxy-ethyl)-4-phenyl-butyl]-3-ethyl-1H-pyrazole-4-carboxamide and 30 mg (0.129 mmol) of methyl 3,4-methylenedioxyphenyl acetate are refluxed for 6 hours in 0.3 ml of a 0.5M ethanolic potassium tert-butoxide solution. After dichloromethane and saturated aqueous sodium hydrogen carbonate solution have been added, the phases are separated. Purification by chromatography gives 3 mg (20%) of a solid, $R_f$=0.65 (dichloromethane/methanol=15:1).

Example 52

6-(3,4-Methylenedioxy-benzyl)-1-[1-(1-hydroxy-ethyl)-4-phenyl-butyl]-1,5-dihydro-pyrazolo[3,4-d]pyrimidin-4-one

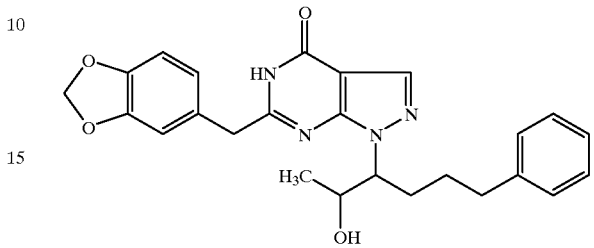

20 mg (0.066 mmol) of 5-amino-1-[1-(1-hydroxy-ethyl)-4-phenyl-butyl]-1H-pyrazole-4-carboxamide and 41 mg (0.210 mmol) of methyl 3,4-methylenedioxyphenylacetate are refluxed for 6 hours in 1.06 ml of a 0.5M ethanolic potassium tert-butoxide solution. After dichloromethane and saturated aqueous sodium hydrogen carbonate solution have been added, the phases are separated. Purification by chromatography gives 19 mg (64%) of a solid, $R_f$=0.20 (dichloromethane/methanol=15:1).

Example 53

6-(3,4-Methylenedioxy-benzyl)-1-[1-(1-hydroxy-ethyl)-4-phenyl-butyl)-3-methyl-1,5-dihydro-pyrazolo[3,4-d]pyrimidin-4-one

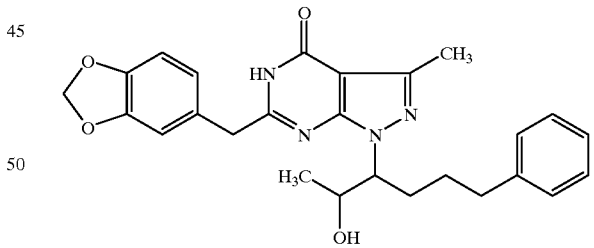

10 mg (0.037 mmol) of 5-amino-1-[1-(1-hydroxy-ethyl)-4-phenyl-butyl]-3-methyl-1H-pyrazole-4-carboxamide and 30 mg (0.129 mmol) of methyl 3,4-methylenedioxyphenylacetate are refluxed for 6 hours in 0.3 ml of a 0.5M ethanolic potassium tert-butoxide solution. After dichloromethane and saturated aqueous sodium hydrogen carbonate solution have been added, the phases are separated. Purification by chromatography gives 5 mg (31%) of a solid, $R_f$=0.44 (dichloromethane/methanol=15:1).

Example 54

6-(3,4-Methylenedioxy-benzyl)-1-(2-octyl)-3-methyl-1,5-dihydro-pyrazolo[3,4-d]pyrimidin-4-one

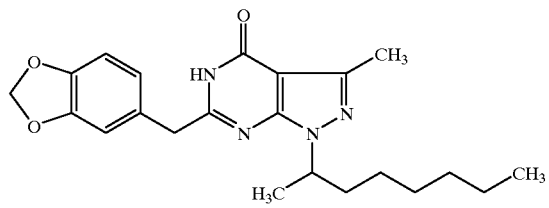

10 mg (0.037 mmol) of 5-amino-3-methyl-1-(2-octyl)-1H-pyrazole-4-carboxamide and 30 mg (0.129 mmol) of methyl 3,4-methylenedioxyphenylacetate are refluxed for 6 hours in 0.3 ml of a 0.5M ethanolic potassium tert-butoxide solution. After dichloromethane and saturated aqueous sodium hydrogen carbonate solution have been added, the phases are separated. Purification by chromatography gives 2 mg (16%) of a solid, $R_f$=0.67 (dichloromethane/methanol=15:1).

Example 55

6-(3,4-Methylenedioxy-benzyl)-1-(2-octyl)-3-ethyl-1,5-dihydro-pyrazolo[3,4-d]pyrimidin-4-one

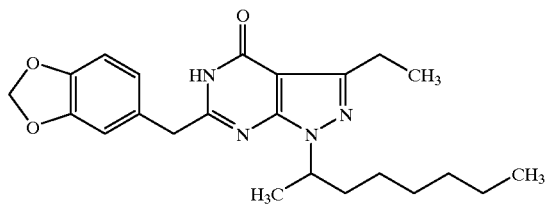

10 mg (0.037 mmol) of 5-amino-3-ethyl-1-(2-octyl)-1H-pyrazole-4-carboxamide and 30 mg (0.129 mmol) of methyl 3,4-methylenedioxyphenylacetate are refluxed for 6 hours in 0.3 ml of a 0.5M ethanolic potassium tert-butoxide solution. After dichloromethane and saturated aqueous sodium hydrogen carbonate solution have been added, the phases are separated. Purification by chromatography gives 4 mg (25%) of a solid, $R_f$=0.76 (dichloromethane/methanol=15:1).

Example 56

6-(3,4-Methylenedioxy-benzyl)-1-(3-nonyl)-3-methyl-1,5-dihydro-pyrazolo[3,4-d]pyrimidin-4-one

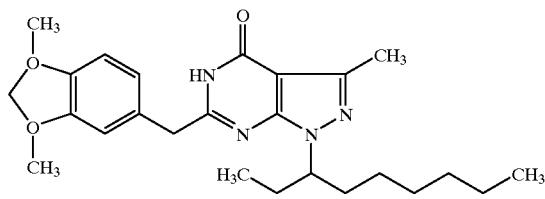

15 mg (0.055 mmol) of 5-amino-3-methyl-1-(3-nonyl)-1H-pyrazole-4-carboxamide and 53 mg (0.274 mmol) of methyl 3,4-methylenedioxyphenylacetate are refluxed for 6 hours in 0.5 ml of a 0.5M ethanolic sodium ethoxide solution. After dichloromethane and saturated aqueous sodium hydrogen carbonate solution have been added, the phases are separated. Purification by chromatography gives 11.8 mg (52%) of a solid, $R_f$=0.65 (dichloromethane/methanol=15:1).

Example 57

6-(3,4-Dimethoxy-benzyl)-1-(3-nonyl)-3-methyl-1,5-dihydro-pyrazolo[3,4-d]pyrimidin-4-one

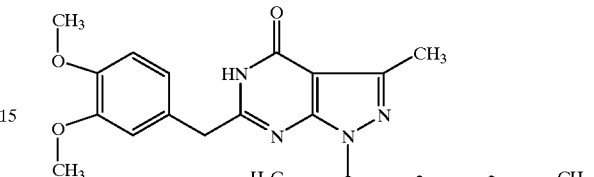

10 mg (0.036 mmol) of 5-amino-3-methyl-(3-nonyl)-1H-pyrazole-4-carboxamide and 57 mg (0.274 mmol) of methyl 3,4-dimethoxyphenylacetate are refluxed for 6 hours in 0.5 ml of a 0.5M ethanolic sodium ethoxide solution. After dichloromethane and saturated aqueous sodium hydrogen carbonate solution have been separated. Purification by chromatography gives 7.3 mg (48%) of a solid, $R_f$=0.57 (dichloromethane/methanol=15:1).

Example 58

6-(3-Chloro-4-methoxy-benzyl)-1-(3-nonyl)-3-methyl-1,5-dihydro-pyrazolo[3,4-d]pyrimidin-4-one

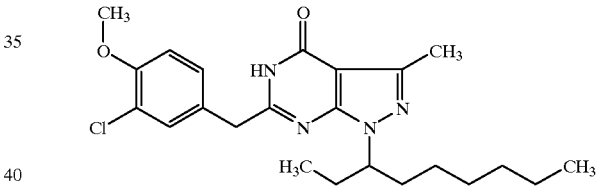

13 mg (0.050 mmol) of 5-amino-3-methyl-1-(3-nonyl)-1H-pyrazole-4-carboxamide and 53 mg (0.248 mmol) of methyl 3-chloro-4-methoxyphenylacetate are refluxed for 6 hours in 0.5 ml of a 0.5M ethanolic sodium ethoxide solution. After dichloromethane and saturated aqueous sodium hydrogen carbonate solution have been added, the phases are separated. Purification by chromatography gives 10 mg (47%) of a solid, $R_f$=0.265 (dichloromethane/methanol=15:1).

Example 59

6-(4-Amino-benzyl)-1-(3-nonyl)-3-methyl-1,5-dihydro-pyrazolo[3,4-d]pyrimidin-4-one

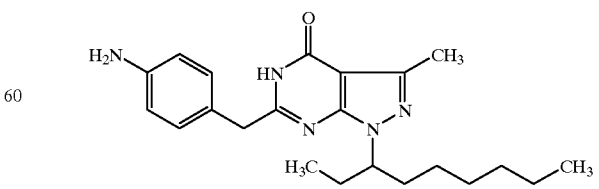

10 mg (0.037 mmol) of 5-amino-3-methyl-1-(3-nonyl)-1H-pyrazole-4-carboxamide and 45 mg (0.274 mmol) of methyl 4-aminophenylacetate are refluxed for 6 hours in 0.5 ml of a 0.5M ethanolic sodium ethoxide solution. After dichloromethane and saturated aqueous sodium hydrogen carbonate solution have been added, the phases are separated. Purification by chromatography gives 4.9 mg (35%) of a solid, $R_f$=0.45 (dichloromethane/methanol=15:1).

sodium ethoxide solution. After dichloromethane and saturated aqueous sodium hydrogen carbonate solution have been added, the phases are separated. Purification by chromatography gives 3.8 mg (16%) of a solid, $R_f$=0.36 (dichloromethane/methanol=15:1).

Example 60

6-(3-ethoxycarbonyl-benzyl)-1-(3-nonyl)-3-methyl-1,5-dihydro-pyrazolo[3,4-d]pyrimidin-4-one

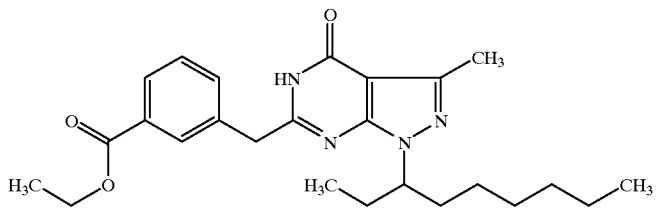

11 mg (0.042 mmol) of 5-amino-3-methyl-1-(3-nonyl)-1H-pyrazole-4-carboxamide and 37 mg (0.167 mmol) of methyl 3-ethoxycarbonylphenylacetate are refluxed for 6 hours in 0.5 ml of a 0.5M ethanolic sodium ethoxide solution. After dichloromethane and saturated aqueous sodium hydrogen carbonate solution have been added, the phases are separated. Purification by chromatography gives 6.8 mg (37%) of a solid, $R_f$=0.47 (dichloromethane/methanol=15:1).

Example 61

6-(3-N-methylaminosulphonyl-benzyl)-1-(3-nonyl)-3-methyl-1,5-dihydro-pyrazolo[3,4-d]pyrimidin-4-one

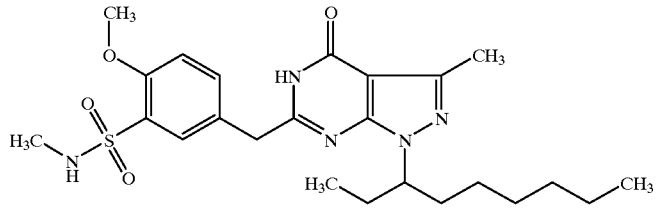

13 mg (0.050 mmol) of 5-amino-3-methyl-1-(3-nonyl)-1H-pyrazole-4-carboxamide and 46 mg (0.167 mmol) of methyl 3-N-methylaminosulphonyl-4-methoxyphenyl acetate are refluxed for 6 hours in 0.5 ml of a 0.5M ethanolic Example 62

6-(4-N-methylpiperazinosulphonyl-benzyl)-1-(3-nonyl)-3-methyl-1,5-dihydro-pyrazolo[3,4-d]pyrimidin-4-one

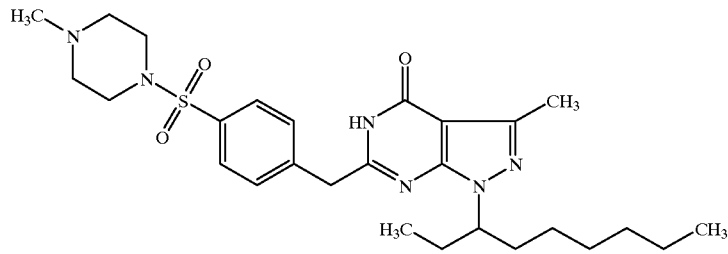

18 mg (0.068 mmol) of 5-amino-3-methyl-1-(3-nonyl)-1H-pyrazole-4-carboxamide and 86 mg (0.274 mmol) of methyl 4-N-methylpiperazinosulphonylphenyl acetate are refluxed for 6 hours in 0.5 ml of a 0.5M ethanolic sodium ethoxide solution. After dichloromethane and saturated aqueous sodium hydrogen carbonate solution have been added, the phases are separated. Purification by chromatography gives 17 mg (47%) of a solid, $R_f$=0.13 (dichloromethane/methanol=15:1).

Example 63

6-(3-chloro-4-methoxy-benzyl)-1-(3-nonyl)-3-methyl-1,5-dihydro-pyrazolo[3,4-d]pyrimidin-4-one

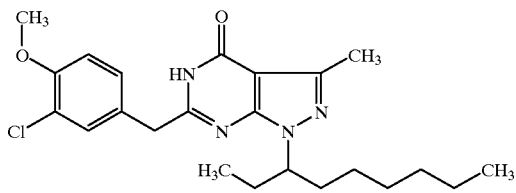

13 mg (0.050 mmol) of 5-amino-3-methyl-1-(3-nonyl)-1H-pyrazole-4-carboxamide and 53 mg (0.248 mmol) of methyl 3-chloro-4-methoxyphenylacetate are refluxed for 6 hours in 0.5 ml of a 0. 5M ethanolic sodium ethoxide solution. After dichloromethane and saturated aqueous sodium hydrogen carbonate solution have been added, the phases are separated. Purification by chromatography gives 10.1 mg (47%) of a solid, $R_f$=0.63 (dichloromethane/methanol=15:1).

Example 64

6-(3,4-methylenedioxy-benzyl)-1-(3-nonyl)-3-ethyl-1,5-dihydro-pyrazolo[3,4-d]pyrimidin-4-one

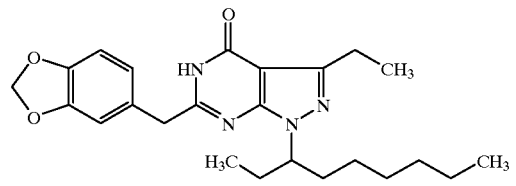

10 mg (0.037 mmol) of 5-amino-3-ethyl-1-(3-nonyl)-1H-pyrazole-4-carboxamide and 30 mg (0.129 mmol) of methyl 3,4-methylenedioxyphenylacetate are refluxed for 6 hours in 0.3 ml of a 0.5M ethanolic potassium tert-butoxide solution. After dichloromethane and saturated aqueous sodium hydrogen carbonate solution have been added, the phases are separated. Purification by chromatography gives 2 mg (11%) of a solid, $R_f$=0.76 (dichloromethane/methanol=15:1).

Example 65

6-(3-chloro-4-methoxy-benzyl)-1-(3-nonyl)-3-ethyl-1,5-dihydro-pyrazolo[3,4-d]pyrimidin-4-one

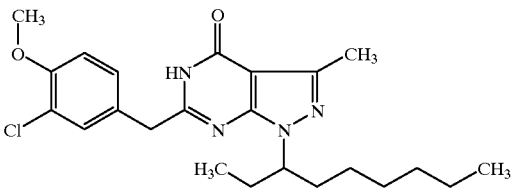

18 mg (0.065 mmol) of 5-amino-3-ethyl-1-(3-nonyl)-1H-pyrazole-4-carboxamide and 69 mg (0.323 mmol) of methyl 3-chloro-4-methoxyphenylacetate are refluxed for 6 hours in 0.5 ml of a 0.5M ethanolic sodium ethoxide solution. After dichloromethane and saturated aqueous sodium hydrogen carbonate solution have been added, the phases are separated. Purification by chromatography gives 8 mg (28%) of a solid, $R_f$=0.75 (dichloromethane/methanol=15:1).

Example 66

6-(3,4-Methylenedioxy-benzyl)-1-(4-decyl)-3-methyl-1,5-dihydro-pyrazolo[3,4-d]pyrimidin-4-one

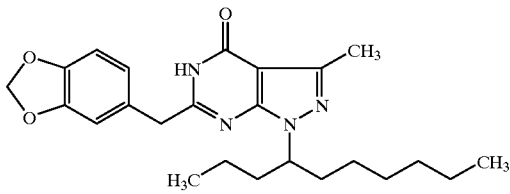

6 mg (0.021 mmol) of 5-amino-3-methyl-1-(4-decyl)-1H-pyrazole-4-carboxamide and 20 mg (0.103 mmol) of methyl 3,4-methylenedioxyphenylacetate are refluxed for 6 hours in 0.3 ml of a 0.5M ethanolic sodium ethoxide solution. After dichloromethane and saturated aqueous sodium hydrogen carbonate solution have been added, the phases are separated. Purification by chromatography gives 5.4 mg (59%) of a solid, $R_f$=0.60 (dichloromethane/methanol=15:1).

Example 67

6-(3,4-Dimethoxy-benzyl)-1-(4-decyl)-3-methyl-1,5-dihydro-pyrazolo[3,4-d]pyrimidin-4-one

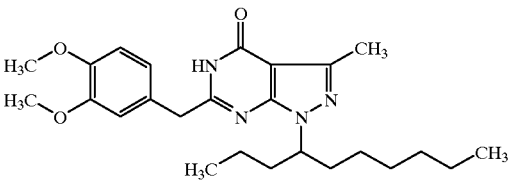

6 mg (0.021 mmol) of 5-amino-3-methyl-1-(4-decyl)-1H-pyrazole-4-carboxamide and 20 mg (0.095 mmol) of methyl 3,4-dimethoxyphenylacetate are refluxed for 6 hours in 0.3 ml of a 0.5M ethanolic potassium tert-butoxide solution. After dichloromethane and saturated aqueous sodium hydrogen carbonate solution have been added, the phases are separated. Purification by chromatography gives 2.4 mg (26%) of a solid, $R_f$=0.66 (dichloromethane/methanol=15:1).

Example 68

6-(3,4,5-trimethoxy-benzyl)-1-(4-decyl)-3-methyl-1,5-dihydro-pyrazolo[3,4-d]pyrimidin-4-one

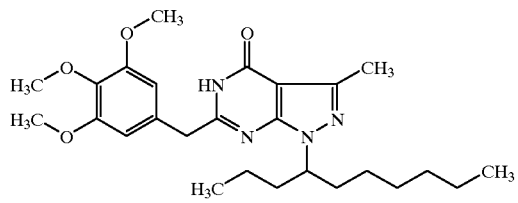

6 mg (0.021 mmol) of 5-amino-3-methyl-1-(4-decyl)-1H-pyrazole-4-carboxamide and 20 mg (0.083 mmol) of methyl 3,4,5-trimethoxyphenylacetate are refluxed for 6 hours in 0.3 ml of a 0.5M ethanolic potassium tert-butoxide solution. After dichloromethane and saturated aqueous sodium hydrogen carbonate solution have been added, the phases are separated. Purification by chromatography gives 2.9 mg (29%) of a solid, $R_f$=0.50 (dichloromethane/methanol=15:1).

Example 69

6-(4-N-methylpiperazinosulphonyl-benzyl)-1-(4-decyl)-3-methyl-1,5-dihydro-pyrazolo[3,4-d]pyrimidin-4-one

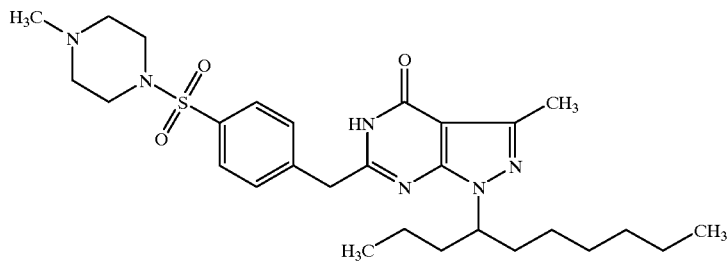

6 mg (0.021 mmol) of 5-amino-3-methyl-1-(4-decyl)-1H-pyrazole-4-carboxamide and 20 mg (0.064 mmol) of methyl 4-N-methylpiperazinosulphonylphenyl acetate are refluxed for 6 hours in 0.3 ml of a 0.5M ethanolic potassium tert-butoxide solution. After dichloromethane and saturated aqueous sodium hydrogen carbonate solution have been added, the phases are separated. Purification by chromatography gives 2 mg (17%) of a solid, $R_f$=0.45 (dichloromethane/methanol=15:1).

Example 70

6-(3,4-Dichloro-benzyl)-1-(4-decyl)-3-ethyl-1,5-dihydro-pyrazolo[3,4-d]pyrimidin-4-one

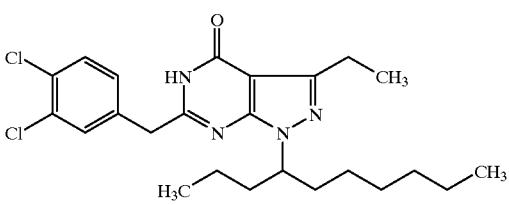

10 mg (0.02 mmol) of 5-amino-3-ethyl-1-(4-decyl)-1H-pyrazole-4-carboxamide and 20 mg (0.091 mmol) of methyl 3,4-dichlorophenylacetate are refluxed for 6 hours in 0.3 ml of a 0.5M ethanolic sodium ethoxide solution. After dichloromethane and saturated aqueous sodium hydrogen carbonate solution have been added, the phases are separated. Purification by chromatography gives 4 mg (45%) of a solid, $R_f$=0.67 (dichloromethane/methanol=15:1).

Example 71

6-(4-Bromo-benzyl)-1-(4-decyl)-3-ethyl-1,5-dihydro-pyrazolo[3,4-d]pyrimidin-4-one

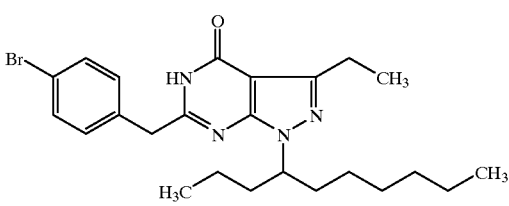

10 mg (0.034 mmol) of 5-amino-3-ethyl-1-(4-decyl)-1H-pyrazole-4-carboxamide and 20 mg (0.087 mmol) of methyl 4-bromophenylacetate are refluxed for 6 hours in 0.3 ml of a 0.5M ethanolic sodium ethoxide solution. After dichloromethane and saturated aqueous sodium hydrogen carbonate solution have been added, the phases are separated. Purification by chromatography gives 7 mg (67%) of a solid, $R_f$=0.69 (dichloromethane/methanol=15:1).

Example 72

6-(3,4-Methylenedioxy-benzyl)-1-(4-decyl)-3-ethyl-1,5-dihydro-pyrazolo[3,4-d]pyrimidin-4-one

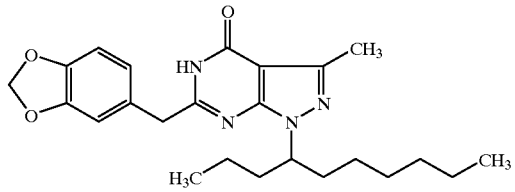

10 mg (0.034 mmol) of 5-amino-3-ethyl-1-(4-decyl)-1H-pyrazole-4-carboxamide and 20 mg (0.103 mmol) of methyl 3,4-methylenedioxyphenylacetate are refluxed for 6 hours in 0.3 ml of a 0.5M ethanolic sodium ethoxide solution. After dichloromethane and saturated aqueous sodium hydrogen carbonate solution have been added, the phases are separated. Purification by chromatography gives 4 mg (48%) of a solid, $R_f$=0.68 (dichloromethane/methanol=15:1).

Example 73

6-(3,4-Dimethoxy-benzyl)-1-(4-decyl)-3-ethyl-1,5-dihydro-pyrazolo[3,4-d]pyrimidin-4-one

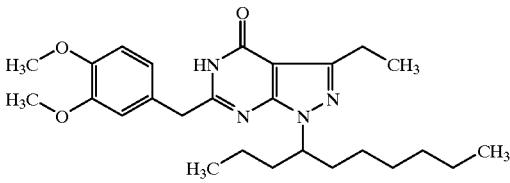

6 mg (0.02 mmol) of 5-amino-3-ethyl-1-(4-decyl)-1H-pyrazole-4-carboxamide and 20 mg (0.095 mmol) of methyl 3,4-dimethoxyphenylacetate are refluxed for 6 hours in 0.3 ml of a 0.5M ethanolic potassium tert-butoxide solution. After dichloromethane and saturated aqueous sodium hydrogen carbonate have been added, the phases are separated. Purification by chromatography gives 4 mg (42%) of a solid, $R_f$=0.47 (dichloromethane/methanol=15:1).

Example 74

6-(3,4,5-Trimethoxy-benzyl)-1-(4-decyl)-3-ethyl-1,5-dihydro-pyrazolo[3,4-d]pyrimidin-4-one

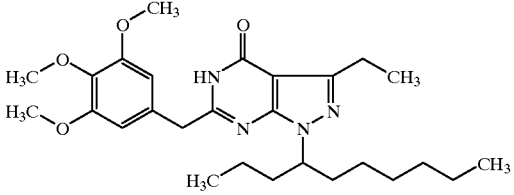

6 mg (0.02 mmol) of 5-amino-3-ethyl-1-(4-decyl)-1H-pyrazole-4-carboxamide and 20 mg (0.083 mmol) of methyl 3,4,5-trimethoxyphenylacetate are refluxed for 6 hours in 0.3 ml of a 0.5M ethanolic potassium tert-butoxide solution. After dichloromethane and saturated aqueous sodium hydrogen carbonate have been added, the phases are separated. Purification by chromatography gives 5.5 mg (55%) of a solid, $R_f$=0.47 (dichloromethane/methanol=15:1).

Example 75

6-(4-N-methylpiperazinosulphonyl-benzyl)-1-(4-decyl)-3-ethyl-1,5-dihydro-pyrazolo[3,4-d]pyrimidin-4-one

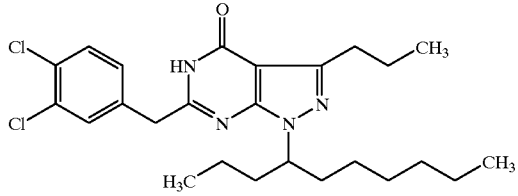

6 mg (0.02 mmol) of 5-amino-3-ethyl-1-(4-decyl)-1H-pyrazole-4-carboxamide and 20 mg (0.064 mmol) of methyl 4-N-methylpiperazinosulphonylphenylacetate are refluxed for 6 hours in 0.3 ml of a 0.5M ethanolic potassium tert-butoxide solution. After dichloromethane and saturated aqueous sodium hydrogen carbonate have been added, the phases are separated. Purification by chromatography gives 4.3 mg (38%) of a solid, $R_f$=0.50 (dichloromethane/methanol=15:1).

Example 76

6-(3,4-Dichloro-benzyl)-1-(4-decyl)-3-propyl-1,5-dihydro-pyrazolo[3,4-d]pyrimidin-4-one

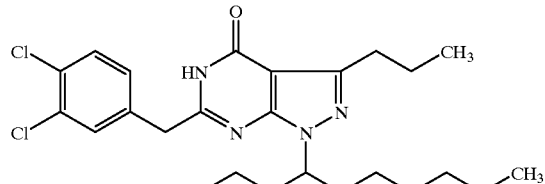

10 mg (0.019 mmol) of 5-amino-3-propyl-1-(4-decyl)-1H-pyrazole-4-carboxamide and 20 mg (0.091 mmol) of methyl 3,4-dichlorophenylacetate are refluxed for 6 hours in 0.3 ml of a 0.5M ethanolic sodium ethoxide solution. After dichloromethane and saturated aqueous sodium hydrogen carbonate solution have been added, the phases are separated. Purification by chromatography gives 5 mg (48%) of a solid, $R_f$=0.70 (dichloromethane/methanol=15:1).

Example 77

6-(4-Bromo-benzyl)-1-(4-decyl)-3-propyl-1,5-dihydro-pyrazolo[3,4-d]pyrimidin-4-one

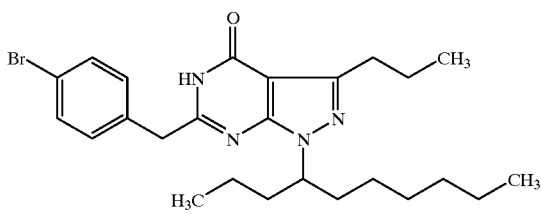

10 mg (0.032 mmol) of 5-amino-3-propyl-1-(4-decyl)-1H-pyrazole-4-carboxamide and 20 mg (0.087 mmol) of methyl 4-bromophenylacetate are refluxed for 6 hours in 0.3 ml of a 0.5M ethanolic sodium ethoxide solution. After dichloromethane and saturated aqueous sodium hydrogen carbonate solution have been added, the phases are separated. Purification by chromatography gives 5 mg (53%) of a solid, $R_f$=0.69 (dichloromethane/methanol=15:1).

Example 78

6-(3,4-Methylenedioxy-benzyl)-1-(4-decyl)-3-propyl-1,5-dihydro-pyrazolo[3,4-d]pyrimidin-4-one

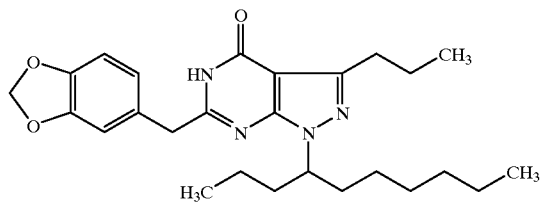

6 mg (0.019 mmol) of 5-amino-3-propyl-1-(4-decyl)-1H-pyrazole-4-carboxamide and 20 mg (0.103 mmol) of methyl 3,4-methylenedioxyphenylacetate are refluxed for 6 hours in 0.3 ml of a 0.5M ethanolic sodium ethoxide solution. After dichloromethane and saturated aqueous sodium hydrogen carbonate solution have been added, the phases are separated. Purification by chromatography gives 4.1 mg (47%) of a solid, $R_f$=0.68 (dichloromethane/methanol=15:1).

Example 79

6-(3,4-Dimethoxy-benzyl)-1-(4-decyl)-3-propyl-1,5-dihydro-pyrazolo[3,4-d]pyrimidin-4-one

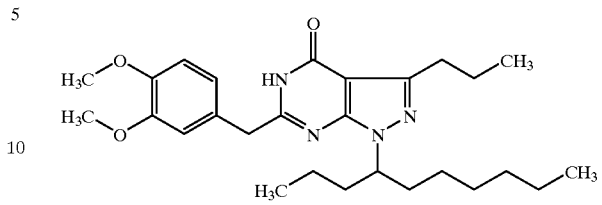

6 mg (0.019 mmol) of 5-amino-3-propyl-1-(4-decyl)-1H-pyrazole-4-carboxamide and 20 mg (0.095 mmol) of methyl 3,4-dimethoxyphenylacetate are refluxed for 6 hours in 0.3 ml of a 0.5M ethanolic potassium tert-butoxide solution. After dichloromethane and saturated aqueous sodium hydrogen carbonate have been added, the phases are separated. Purification by chromatography gives 6.6 mg (68%) of a solid, $R_f$=0.25 (dichloromethane/methanol=15:1).

Example 80

6-(3,4,5-Trimethoxy-benzyl)-1-(4-decyl)-3-propyl-1,5-dihydro-pyrazolo[3,4-d]pyrimidin-4-one

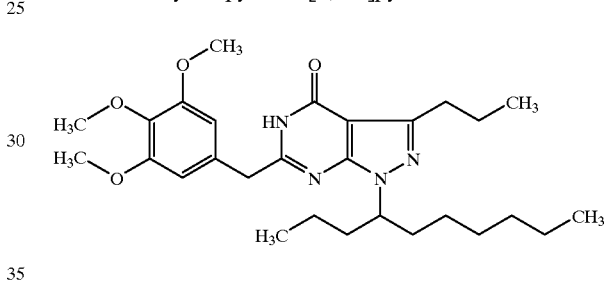

6 mg (0.019 mmol) of 5-amino-3-propyl-1-(4-decyl)-1H-pyrazole-4-carboxamide and 20 mg (0.083 mmol) of methyl 3,4,5-trimethoxyphenylacetate are refluxed for 6 hours in 0.3 ml of a 0.5M ethanolic potassium tert-butoxide solution. After dichloromethane and saturated aqueous sodium hydrogen carbonate have been added, the phases are separated. Purification by chromatography gives 5.1 mg (56%) of a solid, $R_f$=0.17 (dichloromethane/methanol=15:1).

Example 81

6-(4-N-methylpiperazinosulphonyl-benzyl)-1-(4-decyl)-3-propyl-1,5-dihydro-pyrazolo-[3,4-d]pyrimidin-4-one

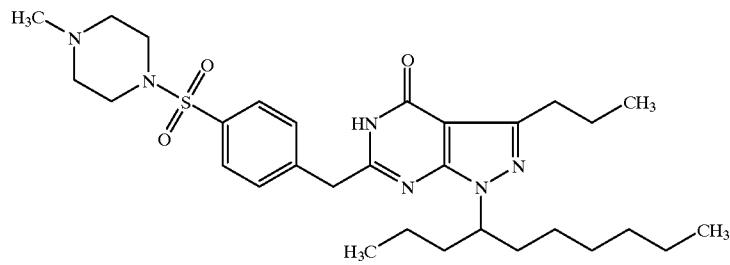

6 mg (0.019 mmol) of 5-amino-3-propyl-1-(4-decyl)-1H-pyrazole-4-carboxamide and 20 mg (0.064 mmol) of methyl 4-N-methylpiperazinosulphonylphenylacetate are refluxed for 6 hours in 0.3 ml of a 0.5M ethanolic potassium tert-butoxide solution. After dichloromethane and saturated aqueous sodium hydrogen carbonate have been added, the phases are separated. Purification by chromatography gives 4 mg (36%) of a solid, $R_f$=0.16 (dichloromethane/methanol= 15:1).

Examples 82 and 83

6-Benzyl-3-ethyl-1-[2-hydroxy-(6-phenyl)-hex-3-yl]-pyrazolo[3,4-d]pyrimidin-4(5H)-one

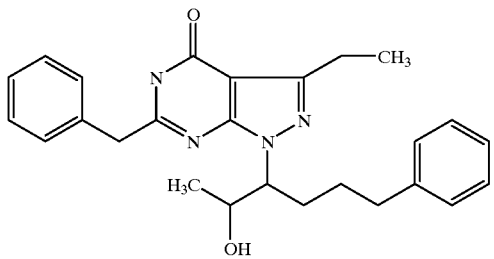

6 mg (0.02 mmol) of 5-amino-4-acetamido-3-ethyl-1-[2-hydroxy-6-phenyl-hex-3-yl]-pyrazole (diastereo mixture) together with approx. 20 mg (0.08 mmol) of phenylacetyl acetate and 0.2 ml (0.1 mmol of 0.5-molar NaOEt in EtOH are refluxed for 1.5 hours under argon. 0.5 ml of dichloromethane and 0.5 ml of 10% strength sodium hydrogen carbonate solution are added to the batch, which is stirred vigorously. The organic phase is separated off and purified by chromatography on silica gel. This gives two fractions:

0.5 mg (=5.8% of theory) of a more unpolar diastereomer of 6-benzyl-3-ethyl-1-[2-hydroxy-(6-phenyl)-hex-3-yl]-pyrozolo[3,4-d]pyrimidin-4(5H)-one (TLC $R_f$-value=0.75; mobile phase: dichloromethane/methanol 10:1; Merck Si60 Art No. 1.05719) and 0.3 mg (=3.5% of theory) of a more polar diastereomer of 6-benzyl-3-ethyl-1-[2-hydroxy-(6-phenyl)-hex-3-yl]-pyrazolo[3,4-d]pyrimidin-4(5H)-one (TLC $R_f$-value= 0.57; mobile phase: dichloromethane/methanol 10:1; Merck Si60 Art No. 1.05719)

Example 84

6-(4-Aminobenzyl)-3-ethyl-1-[2-hydroxy-(6-phenyl)-hex-3-yl]pyrazolo[3,4-d]pyrimidin-4(5H)-one

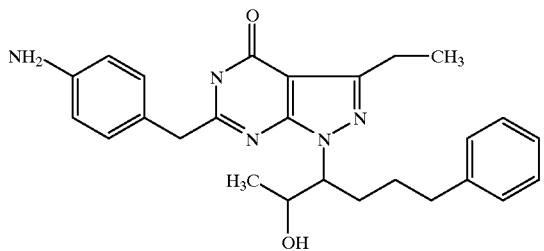

6 mg (0.02 mmol) of 5-amino-4-acetamido-3-ethyl-1-[2-hydroxy-6-phenyl-hex-3-yl]-pyrazole (diastereomer mixture) together with approx. 20 mg (0.08 mmol) of 4-aminophenylacetyl acetate and 0.2 ml (0.1 mmol) of 0.5-molar NaOEt in EtOH are refluxed for 1.5 hours under argon. 0.5 ml of dichloromethane and 0.5 ml of 10% strength sodium hydrogen carbonate solution are added to the batch, which is stirred vigorously. The organic phase is separated off and purified by chromatography on silica gel. This gives a pure fraction:

1.6 mg (=18% of theory) of 6-(4-aminobenzyl)-3-ethyl-1-[2-hydroxy-(6-phenyl)-hex-3-yl]-pyrazolo[3,4-d]pyrimidin-4(5H)one (diastereomer mixture) (TLC $R_f$-value=0.49; mobile phase: dichloromethane/methanol 10:1; Merck Si60 Art. No. 1.05719).

Example 85

6-(4-Morpholinosulphonylbenzyl)-3-ethyl-1-[2-hydroxy-(6-phenyl)-hex-3-yl]-pyrazolo[3,4-d]pyrimidin-4(5H)-one

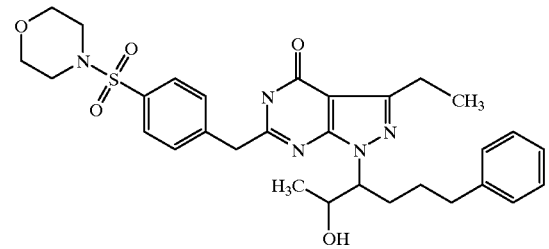

6 mg (0.02 mmol) of 5-amino-4-acetamido-3-ethyl-1-[2-hydroxy-6-phenyl-hex-3-yl]-pyrazole (diastereomer mixture) together with approx. 20 mg (0.08 mmol) of 4-morpholinosulphonylphenylacetyl acetate and 0.2 ml (0.1 mmol) of 0.5-molar NaOEt in EtOH are refluxed for 1.5 hours under argon. 0.5 ml of dichloromethane and 0.5 ml of 10% strength sodium hydrogen carbonate solution are added to the batch, which is stirred vigorously. The organic phase is separated off and purified by chromatography on silica gel. This gives a pure fraction:

2.0 mg (=18% of theory) of 6-(4-morpholinosulphonylbenzyl)-3-ethyl-1-[2-hydroxy-(6-phenyl)-hex-3-yl]-pyrazolo[3,4-d]pyrimidin-4(5H)one (diastereomer mixture) (TLC $R_f$-value=0.61; mobile phase: dichloromethane/methanol 10:1; Merck Si60 Art. No. 1.05719).

What is claimed is:

1. 1,5-Dihydro-pyrazolo[3,4-d]-pyrimidinone derivatives of the general formula (I)

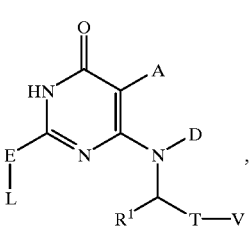

in which

A and D together represent a radical of the formula

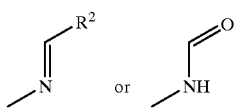

where $R^2$ represents aryl which has 6 to 10 carbon atoms and which is optionally up to trisubstituted by identical or different substituents from the series consisting of nitro, cyano, hydroxyl, trifluoromethyl, halogen, carboxyl, or by straight-chain or branched acyl, alkoxy or alkoxycarbonyl, each of which has up to 6 carbon atoms or hydrogen, trifluoromethyl, cyano, carboxyl, or straight-chain or branched alkoxy or alkoxycarbonyl, each of which has up to 8 carbon atoms, or straight-chain or branched alkyl which has up to 8 carbon atoms and which is optionally substituted by hydroxyl, $R^1$ represents straight-chain or branched acyl having up to 4 carbon atoms, or represents straight-chain or branched alkyl having up to 10 carbon atoms, optionally substituted by hydroxyl, azido or by a group of the formula —$NR^3R^4$ or —$OSO_2R^5$
where
$R^3$ and $R^4$ are identical or different and represent hydrogen or straight-chain or branched alkyl having up to 6 carbon atoms, or
$R^3$ and $R^4$ together with the nitrogen atom form a 5 or 6-membered saturated heterocycle which can optionally contain a further hetero atom selected from the series consisting of S or O or a radical —$NR^6$
where
$R^6$ represent hydrogen or straight-chain or branched alkyl is up to 4 carbon atoms
and
$R^5$ represents phenyl or straight-chain or branched alkyl having up to 5 carbon atoms, E represents a straight-chain or branched alkylene or alkenylene chain, each of which has up to 6 carbon atoms which are optionally substituted by hydroxyl, or represents the C=O group, L and V are identical or different and represent aryl having 6 to 10 carbon atoms or a 5- to 7-membered aromatic, optionally benzo-fused, heterocycle which has up to 3 hetero atoms from the series consisting of S, N and/or O which are optionally up to trisubstituted by identical or different substituents from the series consisting of halogen, hydroxyl, nitro, trifluoromethyl, carboxyl, straight-chain or branched alkyl, alkoxy or alkoxycarbonyl, each of which has up to 6 carbon atoms, or by a group of the formula —$(W)_a$—$NR^7R^8$
where
a is a number 0 or 1,
W is a radical of the formula —CO or —$SO_2$,
$R^7$ and $R^8$ are identical or different and have the abovementioned meaning of $R^3$ and $R^4$,
and/or the cycles are optionally substituted by aryl having 6 to 10 carbon atoms or by a 5- to 7-membered aromatic, optionally benzo-fused, heterocycle having up to 3 hetero atoms from the series consisting of S, N and/or O, which, in turn, are optionally up to disubstituted by identical or different substituents from the series consisting of halogen, hydroxyl, nitro, carboxyl, trifluoromethyl or by straight-chain or branched alkyl, alkox or alkoxycarbonyl, each of which has up to 5 carbon atoms, or by a group of the formula —$(W')_b$—$NR^9R^{10}$
where
b has the abovementioned meaning of a and is identical to this meaning or different from it,
$R^9$ and $R^{10}$ have the abovementioned meaning of $R^3$ and $R^4$ and are identical to this meaning or different from it, W' has the abovementioned meaning of W and is identical to this meaning or different from it, L represents a radical of the formula

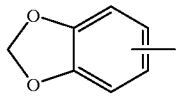

or

T represents a radical of the formula —$CH_2$—X—Y—
where
X represents a bond or an oxygen or sulphur atom or the —NH-group,
Y represents a straight-chain or branched alkylene chain having up to 9 carbon atoms, and the tautomers and salts of these.

2. 1,5-Dihydro-pyrazolo[3,4-d]-pyrimidinone derivatives of the formula according to claim 1
in which
A and D together represent a radical of the formula

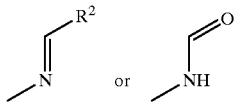

where
$R^2$ represents phenyl which is optionally up to disubstituted by identical or different substituents from the series consisting of nitro, cyano, hxdroxyl, trifluoromethyl, fluorine, chlorine, bromine, carboxyl or by straight-chain or branched acyl, alkoxy or alkoxycarbonyl, each of which has up to 5 carbon atoms, or
hydrogen, trifluoromethyl, cyano, carboxyl, straight-chain or branched alkoxy or alkoxycarbonyl, each of which has up to 6 carbon atoms, or straight-chain or branched alkyl which has up to 6 carbon atoms and which is optionally substituted by hydroxyl, $R^1$ represents straight-chain or branched acyl having up to 6 carbon atoms, or
straight-chain or branched alkyl which has up to 8 carbon atoms and which is substituted by hydroxyl, azido or by a group of the formula —$NR^3R^4$ or O—$SO_2$—$R^5$
in which
$R^3$ and $R^4$ are identical or different and represent hydrogen or straight-chain or branched alkyl having up to 5 carbon atoms, or
$R^3$ and $R^4$ together with the nitrogen atom form a morpholinyl-piperidinyl or piperazinyl ring, the latter optionally being substituted via the nitrogen function by straight-chain or branched alkyl having up to 3 carbon atoms,
and
$R^5$ represents phenyl or straight-chain or branched alkyl having up to 4 carbon atoms, E represents a straight-chain or branched alkylene or alkenylene chain, each of which has up to 5 carbon atoms and each of which is optionally substituted by hydroxyl, or represents the C=O group, L and V are identical or different and represent phenyl, naphthyl, pyridyl, thienyl, indolyl or furyl, each of which is up to trisubstituted by identical or different substituents from the series consisting of fluorine, chlorine, bromine, trifluoromethyl, hydroxyl, nitro, carboxyl, straight-chain or branched alkyl, alkoxy or alkoxycarbonyl, each of which has up to 5 carbon atoms, or by a group of the formula —$(W)_a NR^7 R^8$
in which
a represents a number 0 or 1,
W represents a radical of the formula —CO or —$SO_2$,
$R^7$ and $R^8$ are identical or different and have the abovementioned meaning of $R^3$ and $R^4$,
and/or the cycles are optionally substituted by naphthyl, phenyl, pyridyl, indolyl, thienyl or furyl, optionally by phenyl, naphthyl, pyridyl, thienyl, furyl, pyrryl or pyrimidyl, which, in turn, are optionally substituted by fluorine, chlorine, bromine, hydroxyl, nitro, carboxyl, trifluoromethyl or straight-chain or branched alkyl, alkoxy or alkoxycarbonyl, each of which has up to 3 carbon atoms, or by a group of the formula —$(W')_b NR^9 R^{10}$
in which
b has the abovementioned meaning of a and is identical to this meaning or different from it,
W' has the abovementioned meaning of W and is identical to this meaning or different from it,
$R^9$ and $R^{10}$ have the abovementioned meaning of $R^3$ and $R^4$,
or
L represents a radical of the formula

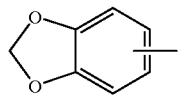

T represents a radical of the formula —$CH_2$—X—Y—
in which
X represents a bond or an oxygen or sulphur atom or the —NH-group,
Y represents a straight-chain or branched alkylene chain having up to 8 carbon atoms,
and the tautomers and salts of these.

3. 1,5-Dihydro-pyrazolo[3,4-d]-pyrimidinone derivatives of the formula (I) according to claim 1
in which
A and D together represent a radical of the formula

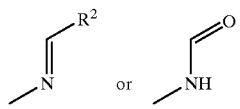

in which
$R^2$ represents phenyl which is optionally up to disubstituted by identical or different substituents from the series consisting of nitro, cyano, hxdroxyl, trifluoromethyl, fluorine, chlorine, bromine, carboxyl or by straight-chain or branched acyl, akoxy or alkoxycarbonyl, each of which has up to 4 carbon atoms, or
represents hydrogen, trifluoromethyl, cyano, carboxyl, straight-chain or branched alkoxy or alkoxycarbonyl, each of which has up to 5 carbon atoms, or straight-chain or branched alkyl which has up to 5 carbon atoms and which is optionally substituted by hydroxyl, $R^1$ represents straight-chain or branched acyl having up to 5 carbon atoms, or
straight-chain or branched alkyl which has up to 6 carbon atoms and which is substituted by hydroxyl, azido or by a group of the formula —$NR^3 R^4$ or O—$SO_2 R^5$
in which
$R^3$ and $R^4$ are identical or different and represent hydrogen or straight-chain or branched alkyl having up to 4 carbon atoms, or
$R^3$ and $R^4$ together with the nitrogen atom form a morpholinyl, piperdinyl or piperazinyl ring, the latter optionally being methyl-substituted via the nitrogen function,
and
$R^5$ represents phenyl or straight-chain or branched alkyl having up to 3 carbon atoms,
E represents a straight-chain or branched alkylene or alkenylene chain, each of which has up to 5 carbon atoms which are optionally substituted by hydroxyl, or represents the C=O group,
L and V are identical or different and represent phenyl, naphthyl, furyl, thienyl, indolyl or pyridyl, each of which is optionally up to trisubstituted by identical or different substituents from the series consisting of fluorine, chlorine, bromine, hydroxyl, nitro, carboxyl, straight-chain or branched alkyl, alkoxy or alkoxycarbonyl, each of which has up to 4 carbon atoms, or by a group of the formula —$(W)_a NR^7 R^8$
in which
a represents a number 0 or 1,
W represents a radical of the formula —CO or —$SO_2$,
$R^7$ and $R^8$ are identical or different and have the abovementioned meaning of $R^3$ and $R^4$,
and/or the cycles are optionally substituted by phenyl, pyridyl, thienyl or furyl, which, in turn, are optionally substituted by fluorine, chlorine, bromine, hydroxyl, nitro, carboxyl, trifluoromethyl or by straight-chain or branched alkyl, alkoxy or alkoxycarbonyl, each of which has up to 3 carbon atoms, or by a group of the formula —$(W')_b NR^9 R^{10}$
in which
b has the abovementioned meaning of a and is identical to this meaning or different from it,
W' has the abovementioned meaning of W and is identical to this meaning or different from it,
$R^9$ and $R^{10}$ have the abovementioned meaning of $R^3$ and $R^4$,
or
L represents a radical of the formula

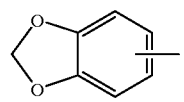

T represents a radical of the formula —$CH_2$—X—Y—
in which
X represents a bond or an oxygen or sulphur atom or the —NH-group,
Y represents a straight-chain or branched alkylene chain having up to 6 carbon atoms,
and the tautomers and salts of these.

4. Process for the preparation of 1,5-dihydro-pyrazolo[3,4-d]-pyrimidinone derivatives according to claim 1, characterized in that

[A] in the event that A and D together represent the radical of the formula

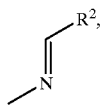

compounds of the general formula (II)

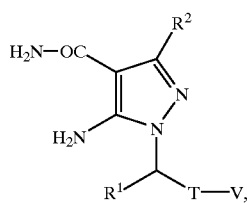
(II)

in which
R$^1$, R$^2$, T and V have the abovementioned meaning
are firstly converted into the compounds of the general formula (IV)

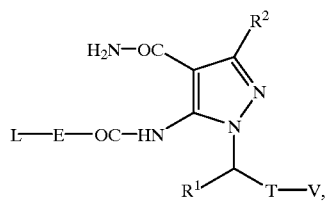
(IV)

in which
E, L, T, V, R$^1$ and R$^2$ have the abovementioned meaning
by reacting them, in inert solvents and in the presence of a base, with compounds of the general formula (III)

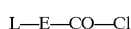
L—E—CO—Cl     (III)

in which
E and L have the abovementioned meaning
and subsequently cyclizing the product with bases,
or
[B] compounds of the general formula (II) are reacted, with direct cyclization, with compounds of the general formula (IIIa)

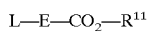
L—E—CO$_2$—R$^{11}$     (IIIa)

in which
E and L have the abovementioned meaning
and
R$^{11}$ represents methyl or ethyl,
and, in a second step, the product is cyclized in inert solvents and in the presence of a base,
or

[C] compounds of the general formula (V)

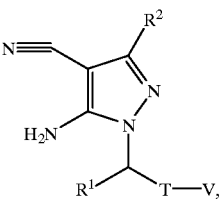
(V)

in which
R$^1$, R$^2$, T and V have the abovementioned meaning
are first reacted with compounds of the general formula (III) in inert solvent and in the presence of a base to give the compounds of the general formula (VI)

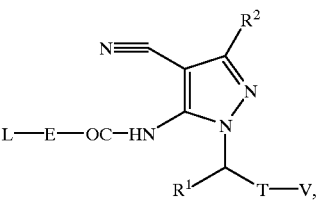
(VI)

in which
R$^1$, R$^2$, E, L, T and V have the abovementioned meaning,
and, in a 2nd step, cyclizing the product in inert solvents and in the presence of a base and of an oxidant,
or
[D] in the event that A and D together represent the radical of the formula

the corresponding compounds of the general formula (I) in which R$^2$ represents methoxy is reacted in the system sodium iodide/trimethylchlorosilane in inert solvents,
and, if appropriate, the substituents mentioned under R$^1$ are introduced or derivatized by subsequent reactions such as acylation, oxidation, substitution and/or reductions,
and, equally, the substituents mentioned above under L and V are introduced and/or varied by customary methods.

5. A pharmaceutical composition comprising at least one 1,5-dihydro-pyrazolo [3,4-d]-pyrimidinone derivative according to claim 1 and a pharmacologically acceptable formulation auxiliary.

6. A method of treating a cardiovascular disease comprising administering to a patient an effective amount therefor of at least one 1,5-dihydro-pyrazolo [3,4-d]-pyrimidinone according to claim 1.

7. A method of treating a cerebrovascular disease comprising administering to a patient an effective amount therefor of at least one 1,5-dihydro-pyrazolo [3,4-d]-pyrimidinone according to claim 1.

8. A method of treating a disease of the peripheral blood vessels comprising administering to a patient an effective amount therefor of at least one 1,5-dihydro-pyrazolo [3,4-d]-pyrimidinone according to claim 1.

9. A method of treating a disease of the urogenital tract comprising administering to a patient an effective amount therefor of at least one 1,5-dihydro-pyrazolo [3,4-d]-pyrimidinone according to claim 1.

* * * * *